US012629518B2

(12) United States Patent
Dixit et al.

(10) Patent No.: US 12,629,518 B2
(45) Date of Patent: May 19, 2026

(54) EXTERNAL NEUROSTIMULATOR

(71) Applicant: NEVRO CORP., Redwood City, CA (US)

(72) Inventors: Apratim Dixit, Redwood City, CA (US); Ivan Tzvetanov, Kailua-Kona, HI (US); Cameron Karamian, Coto de Caza, CA (US); Ivan Wei Tai Lin, San Carlos, CA (US)

(73) Assignee: Globus Medical Inc., Audubon, PA (US)

( * ) Notice: Subject to any disclaimer, the term of this patent is extended or adjusted under 35 U.S.C. 154(b) by 322 days.

(21) Appl. No.: 18/256,132

(22) PCT Filed: Mar. 25, 2022

(86) PCT No.: PCT/US2022/021939
§ 371 (c)(1),
(2) Date: Jun. 6, 2023

(87) PCT Pub. No.: WO2022/204509
PCT Pub. Date: Sep. 29, 2022

(65) Prior Publication Data
US 2024/0033512 A1     Feb. 1, 2024

Related U.S. Application Data

(60) Provisional application No. 63/166,685, filed on Mar. 26, 2021.

(51) Int. Cl.
*A61N 1/36* (2006.01)
*A61N 1/05* (2006.01)
*A61N 1/375* (2006.01)

(52) U.S. Cl.
CPC ....... *A61N 1/36017* (2013.01); *A61N 1/0551* (2013.01); *A61N 1/36062* (2017.08); *A61N 1/3752* (2013.01)

(58) Field of Classification Search
CPC .............. A61N 1/36017; A61N 1/0551; A61N 1/36062; A61N 1/3752; A61N 1/375
See application file for complete search history.

(56) References Cited

U.S. PATENT DOCUMENTS 4,931,039 A * 6/1990 Coe ....................... A61M 25/06
604/9
8,401,670 B2 3/2013 Mehdizadeh et al.
(Continued)

FOREIGN PATENT DOCUMENTS

WO 2020037228 A1 2/2020

OTHER PUBLICATIONS

International Search Report and Written Opinion issued Aug. 15, 2022 in Intl. Appl. No. PCT/US2022/021939.
(Continued)

*Primary Examiner* — Paula J Stice

(57) ABSTRACT

An external neurostimulator includes a housing including a base housing and a top housing, a power source, a pulse generator, and a first and second series of spring-loaded pins electrically coupled to the pulse generator. The top housing includes a central portion, a first side door hingedly coupled to a first side of the central portion, and a second side door hingedly coupled to a second side of the central portion. Each of the first side door and the second side door include a channel formed thereon that is configured to directly receive a proximal end portion of an implantable lead. Each channel includes a series of longitudinally spaced-apart openings formed on the first side door and the second side door, respectively. The first and second series of spring-loaded pins extend through the series of longitudinally spaced-apart openings of the channel on the first and second side doors, respectively.

14 Claims, 16 Drawing Sheets

(56)     References Cited

U.S. PATENT DOCUMENTS

| | | | |
|---|---|---|---|
| 8,996,128 | B2 | 3/2015 | Parker et al. |
| 9,789,321 | B2 | 10/2017 | Dixit et al. |
| 10,154,922 | B1 * | 12/2018 | Perez ................... A61N 1/0502 |
| 2002/0143376 | A1 * | 10/2002 | Chinn ...................... A61N 1/05 607/115 |
| 2006/0167522 | A1 | 7/2006 | Malinowski |
| 2011/0071593 | A1 * | 3/2011 | Parker .................. A61N 1/0553 607/46 |
| 2013/0325092 | A1 | 12/2013 | Parker et al. |
| 2014/0148838 | A1 | 5/2014 | Chase et al. |
| 2015/0100106 | A1 * | 4/2015 | Shishilla .............. A61N 1/3615 607/2 |
| 2016/0067502 | A1 | 3/2016 | Bornzin et al. |
| 2016/0106950 | A1 | 4/2016 | Vasapollo |
| 2017/0332924 | A1 | 11/2017 | Mehdizadeh et al. |
| 2019/0105501 | A1 | 4/2019 | Howard et al. |
| 2020/0346021 | A1 * | 11/2020 | Nageri ................. A61N 1/3752 |

OTHER PUBLICATIONS

Extended European Search Report issued Jul. 3, 2024 in EP Appl. No. 22 776 722.5.

* cited by examiner

EXTERNAL NEUROSTIMULATOR

FIELD OF THE INVENTION

The present disclosure is directed generally to external stimulators, and associated systems and methods.

BACKGROUND OF THE INVENTION

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. In pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation.

One problem associated with existing stimulation systems and methods is that the practitioner may not initially implant the SCS lead in the optimal position. Accordingly, practitioners typically make small adjustments to the position of the implanted lead while the patient is in the operating room. The practitioner then applies stimulation to the lead via an external stimulator, which is temporarily attached to the lead while the lead still extends out of the patient's body. This process is repeated until the practitioner determines the position of the lead that is expected to produce the best patient result. The patient and practitioner can also use the external stimulator during a post-operative trial period, to optimize the characteristics of the applied signal before an implantable pulse generator is connected to the lead and implanted beneath the patient's skin.

To facilitate the foregoing process of alternately providing stimulation to the patient and moving the implanted portion of the lead, manufacturers have developed cables with releasable connectors. Accordingly, the practitioner can connect the cable to the external stimulator and the lead, apply the stimulation, then disconnect the cable, move the lead, and reconnect the cable with the lead in the new position. As noted above, this process can be repeated, as needed, until the desired lead location is obtained.

One drawback with the foregoing approach is that it may be difficult for the practitioner to repeatedly manipulate the connector that attaches the cable to the lead, while still maintaining control over the position of the lead. Additionally, over-manipulation of the connector may inadvertently break the connector. Another drawback is that the connectors, which are outside the patient's body, may be awkward and/or cumbersome for the patient during the post-operative trial period. Accordingly, there remains a need for improved techniques and systems for releasably connecting implanted patient leads to external stimulation devices.

BRIEF SUMMARY OF THE INVENTION

According to a first embodiment hereof, the present disclosure provides an external neurostimulator that includes a housing, a power source disposed within the housing, a pulse generator disposed within the housing and electrically coupled to the power source, and a first series and a second series of spring-loaded pins electrically coupled to the pulse generator. The housing includes a base housing and a top housing. The base housing includes a surface configured to contact a patient's skin. The top housing includes a central portion, a first side door hingedly coupled to a first side of the central portion, and a second side door hingedly coupled to a second side of the central portion. Each of the first side door and the second side door include a channel formed thereon that is configured to directly receive a proximal end portion of an implantable lead. Each channel includes a series of longitudinally spaced-apart openings formed on the first side door and the second side door, respectively. The first series of spring-loaded pins extend through the series of longitudinally spaced-apart openings of the channel on the first side door and the second series of spring-loaded pins extend through the series of longitudinally spaced-apart openings of the channel on the second side door.

In an aspect of the first embodiment, and in combination with any other aspects herein, the disclosure provides that each of the first side door and the second side door has a locked configuration and an unlocked configuration.

In an aspect of the first embodiment, and in combination with any other aspects herein, the disclosure provides that the central portion of the top housing includes a first tab and a second tab, the first and second tabs opposing each other and including a hook formed on outermost end thereof. In the locked configuration of the first side door, the hook of the first tab is received within a recess formed on an inner surface of the first side door. In the locked configuration of the second side door, the hook of the second tab is received within a recess formed on an inner surface of the second side door.

In an aspect of the first embodiment, and in combination with any other aspects herein, the disclosure provides that each of the first side door and the second side door include a latch having an opening formed therethrough, each latch extending towards the base housing. The base housing includes a first post extending outwardly therefrom and a second post extending outwardly therefrom, the latch of the first side door being configured to receive the first post and the latch of the second side door being configured to receive the second post.

In an aspect of the first embodiment, and in combination with any other aspects herein, the disclosure provides that the opening of each latch includes a top circular portion, a bottom circular portion, and a waisted portion disposed between the top and bottom circular portion. In the locked configuration of the first side door, the first post is disposed in the top circular portion of the opening of the latch of the first side door. In the locked configuration of the second side door, the second post is disposed in the top circular portion of the opening of the latch of the second side door. In the unlocked configuration of the first side door, the first post is disposed in the bottom circular portion of the opening of the latch of the first side door. In the unlocked configuration of the second side door, the second post is disposed in the bottom circular portion of the opening of the latch of the second side door.

In an aspect of the first embodiment, and in combination with any other aspects herein, the disclosure provides that a boss is formed on each of the first tab and the second tab, each boss being configured to apply pressure onto the proximal end portion of the implantable lead when the first side door or the second side door, respectively, is in the locked configuration.

In an aspect of the first embodiment, and in combination with any other aspects herein, the disclosure provides that a top surface of each boss is curved.

In an aspect of the first embodiment, and in combination with any other aspects herein, the disclosure provides that the base housing includes a first snap fit feature and a second snap fit feature extending therefrom, the first snap fit feature configured to mate with an opening formed on an underside surface of the first tab of the central portion and the second snap fit feature configured to mate with an opening formed on an underside surface of the second tab of the central portion.

In an aspect of the first embodiment, and in combination with any other aspects herein, the disclosure provides that the channel for each of the first side door and the second side door includes a first end and a second end opposing the first end, the first end being configured as a lead insertion entry point. The first end of the channel for each of the first side door and the second side door includes a horseshoe-shaped surface protrusion formed adjacent thereto.

In an aspect of the first embodiment, and in combination with any other aspects herein, the disclosure provides that the channel for each of the first side door and the second side door includes a first end, a second end opposing the first end, and a notch formed between the first end and the second end, the notch extending outwardly from a longitudinal axis of the channel and being configured as a lead depth indicator point.

In an aspect of the first embodiment, and in combination with any other aspects herein, the disclosure provides that the channel for each of the first side door and the second side door includes a circular portion configured to receive the proximal portion of the implantable lead and a trapezoidal portion configured to receive a stylet.

In an aspect of the first embodiment, and in combination with any other aspects herein, the disclosure provides that each spring-loaded pin of the first series and the second series of spring-loaded pins is configured to contact a connection contact of the proximal portion of the implantable lead.

In an aspect of the first embodiment, and in combination with any other aspects herein, the disclosure provides that the housing has a height of between 18 mm and 22 mm.

In an aspect of the first embodiment, and in combination with any other aspects herein, the disclosure provides that the base housing has a curved perimeter.

In an aspect of the first embodiment, and in combination with any other aspects herein, the disclosure provides that the base housing includes at least one press fit feature configured to mate with an opening formed on an underside surface of the central portion of the top housing such that the base housing is attached to the top housing via the press fit feature.

According to a second embodiment hereof, the present disclosure provides a device that includes a housing and a first series and a second series of spring-loaded pins disposed within the housing. The housing includes a base housing and a top housing. The top housing includes a central portion, a first side door hingedly coupled to a first side of the central portion, and a second side door hingedly coupled to a second side of the central portion. Each of the first side door and the second side door include a channel formed thereon that is configured to receive a portion of an implantable lead. Each channel includes a series of longitudinally spaced-apart openings formed on the first side door and the second side door, respectively. The central portion of the top housing includes a first tab and a second tab, the first and second tabs opposing each other and including a hook formed on outermost end thereof. The first series of spring-loaded pins extend through the series of longitudinally spaced-apart openings of the channel on the first side door and the second series of spring-loaded pins extend through the series of longitudinally spaced-apart openings of the channel on the second side door. Each of the first side door and the second side door has a locked configuration and an unlocked configuration. In the locked configuration of the first side door, the hook of the first tab is received within a recess formed on an inner surface of the first side door. In the locked configuration of the second side door, the hook of the second tab is received within a recess formed on an inner surface of the second side door.

In an aspect of the second embodiment, and in combination with any other aspects herein, the disclosure provides that each of the first side door and the second side door include a latch having an opening formed therethrough. Each latch extends towards the base housing. The base housing includes a first post extending outwardly therefrom and a second post extending outwardly therefrom. The latch of the first side door is configured to receive the first post and the latch of the second side door is configured to receive the second post.

In an aspect of the second embodiment, and in combination with any other aspects herein, the disclosure provides that the opening of each latch includes a top circular portion, a bottom circular portion, and a waisted portion disposed between the top and bottom circular portion. In the locked configuration of the first side door, the first post is disposed in the top circular portion of the opening of the latch of the first side door. In the locked configuration of the second side door, the second post is disposed in the top circular portion of the opening of the latch of the second side door. In the unlocked configuration of the first side door, the first post is disposed in the bottom circular portion of the opening of the latch of the first side door. In the unlocked configuration of the second side door, the second post is disposed in the bottom circular portion of the opening of the latch of the second side door.

In an aspect of the second embodiment, and in combination with any other aspects herein, the disclosure provides that a boss is formed on each of the first tab and the second tab. Each boss is configured to apply pressure onto the implantable lead when the first side door or the second side door, respectively, is in the locked configuration.

In an aspect of the second embodiment, and in combination with any other aspects herein, the disclosure provides that base housing includes a first snap fit feature and a second snap fit feature extending therefrom. The first snap fit feature is configured to mate with an opening formed on an underside surface of the first tab of the central portion and the second snap fit feature is configured to mate with an opening formed on an underside surface of the second tab of the central portion.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 15C is a top view of the first side door of the external neurostimulator of FIG. 3, wherein the first side door is shown removed from the external neurostimulator for sake of illustration only.

FIG. 15D is a bottom view of the first side door of the external neurostimulator of FIG. 3, wherein the first side door is shown removed from the external neurostimulator for sake of illustration only.

DETAILED DESCRIPTION OF THE INVENTION

Specific embodiments of the present invention are now described with reference to the figures, wherein like reference numbers indicate identical or functionally similar elements. The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Aspects of the present disclosure are directed generally to an external stimulator and/or other device positioned external to a patient that is configured to attach or connect to implanted leads or other implanted signal delivery elements. Several aspects of the disclosure are described in the context of a spinal cord stimulation (SC S) system for purposes of illustration. In other embodiments, the disclosed systems and methods may be used in the context of other patient treatment and/or patient diagnostic systems. Several embodiments of representative systems and methods are described below with reference to FIGS. 3-23. A person skilled in the relevant art will understand, however, that the disclosure may have additional embodiments, and/or that aspects of the disclosure may be practiced without several of the details of the embodiments described below.

Figure 1:
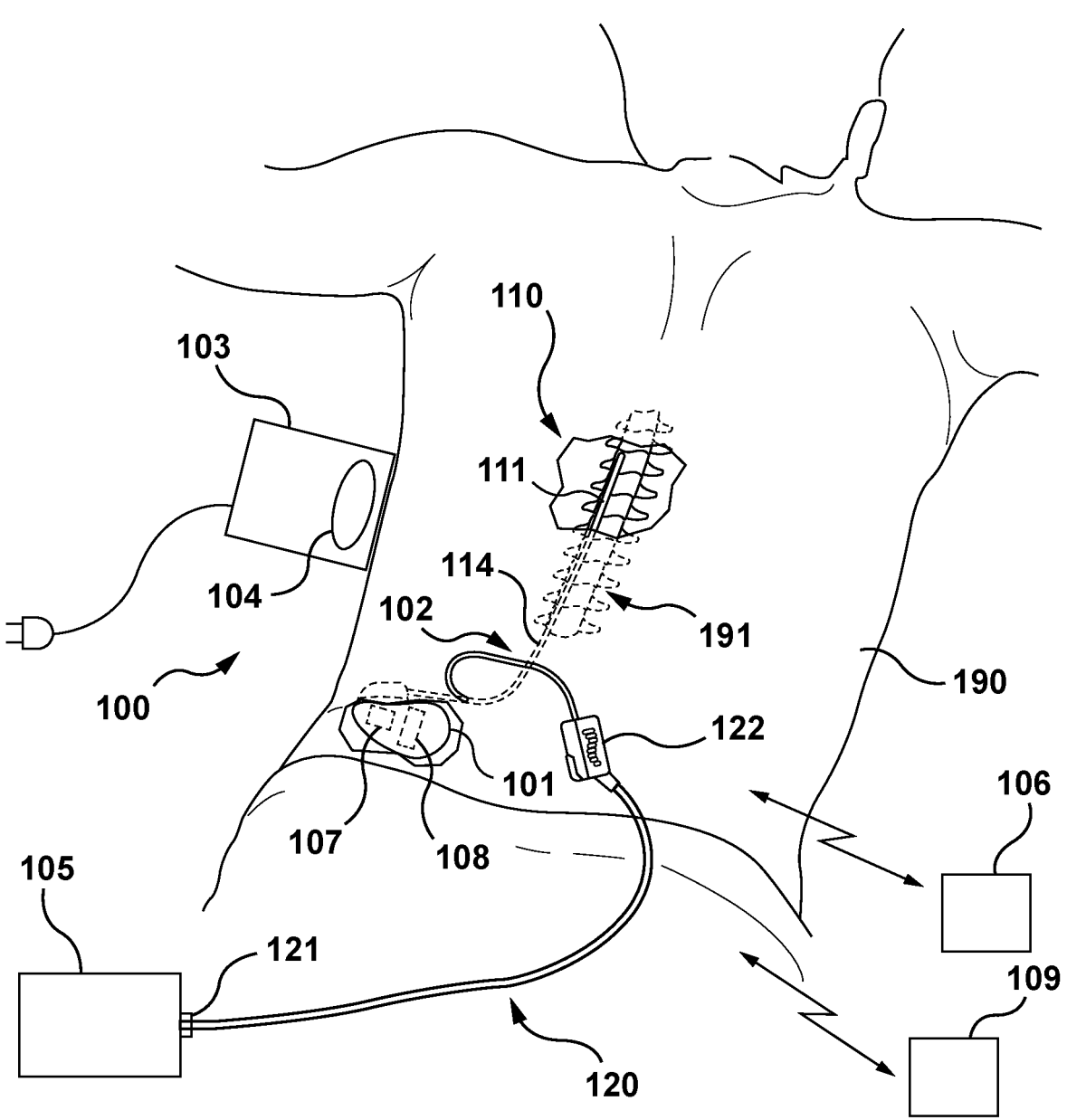
FIG. 1 is a partially schematic illustration of an implantable spinal cord stimulation system positioned at the spine to deliver a therapeutic signal in accordance with an embodiment of the present disclosure.

FIG. 1 schematically illustrates a representative treatment system 100 for providing relief from chronic pain and/or other conditions, arranged relative to the general anatomy of a patient's spinal cord 191. The system 100 can include a pulse generator 101, which may be implanted subcutaneously within a patient 190 and coupled to a signal delivery element 110. In a representative example, the signal delivery element 110 includes a lead or lead body 111 that carries features or elements for delivering therapy to the patient 190 after implantation. The pulse generator 101 can be connected directly to the lead 111, or it can be coupled to the lead 111 via a communication link 102 (e.g., an extension).

Accordingly, the lead 111 can include a terminal section that is releasably connected to an extension at a break 114 (shown schematically in FIG. 1). This allows a single type of terminal section to be used with patients of different body types (e.g., different heights). As used herein, the terms lead and lead body include any of a number of suitable substrates and/or support members that carry devices for providing therapy signals to the patient 190. For example, the lead 111 can include one or more electrodes or electrical contacts that direct electrical signals into the patient's tissue, such as to provide for patient relief. In other embodiments, the signal delivery element 110 can include devices other than a lead body (e.g., a paddle) that also direct electrical signals and/or other types of signals to the patient 190.

The pulse generator 101 can transmit signals to the signal delivery element 110 that up-regulate (e.g., stimulate or excite) and/or down-regulate (e.g., block or suppress) target nerves. As used herein, and unless otherwise noted, the terms "stimulate," "stimulation," and more generally, "modulation," refer to signals that have either type of effect on the target nerves. The pulse generator 101 can include a machine-readable (e.g., computer-readable) medium containing instructions for generating and transmitting suitable therapy signals. The pulse generator 101 and/or other elements of the system 100 can include one or more processors 107, memories 108 and/or input/output devices. Accordingly, the process of providing stimulation signals and executing other associated functions can be performed by computer-executable instructions contained on computer-readable media, e.g., at the processor(s) 107 and/or memory(s) 108. The pulse generator 101 can include multiple portions, elements, and/or subsystems (e.g., for directing signals in accordance with multiple signal delivery parameters), housed in a single housing, as shown in FIG. 1, or in multiple housings.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

In another embodiment, the pulse generator 101 can obtain the power to generate therapy signals from an internal power source, in addition to or in lieu of the external power source 103. For example, the implanted pulse generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In many cases, a trial or external neurostimulator 105 is coupled to the signal delivery element 110 during an initial implant procedure, prior to implanting the pulse generator 101. For example, a practitioner (e.g., a physician and/or a company representative) can use the external neurostimulator 105 to vary the signal delivery parameters provided to the signal delivery element 110 in real time, and select optimal or particularly efficacious parameters. These parameters can include the position of the signal delivery element 110, as well as the characteristics of the electrical signals provided to the signal delivery element 110. In the representative process shown in FIG. 1, the practitioner uses a cable assembly 120 to temporarily connect the external neurostimulator 105 to the signal delivery device 110. The cable assembly 120 can accordingly include a first connector 121 that is releasably connected to the external neurostimulator 105, and a second connector 122 that is releasably connected to the signal delivery element 110. The practitioner can test the efficacy of the signal delivery element 110 in an initial position. The practitioner can then disconnect the cable assembly 120, reposition the signal delivery element 110, and reapply the electrical stimulation. This process can be performed iteratively until the practitioner obtains the desired position for the signal delivery device 110. Optionally, the practitioner may move the partially implanted signal delivery element 110 without disconnecting the cable assembly 120. In either embodiment, the practitioner will connect and disconnect the cable assembly 120 at least once during the process.

After the position of the signal delivery element 110 and appropriate signal delivery parameters are established using the external neurostimulator 105, the patient 190 can receive therapy via signals generated by the external neurostimulator 105, generally for a limited period of time. In a representative application, the patient 190 receives such therapy for a one-week trial period. During this time, the patient wears the cable assembly 120 and the external neurostimulator 105 outside the body. Assuming the trial therapy is effective or shows the promise of being effective, the practitioner then replaces the external neurostimulator 105 with the implanted pulse generator 101, and programs the pulse generator 101 with parameters selected based on the experience gained during the trial period. Optionally, the practitioner can also replace the signal delivery element 110. Once the implantable pulse generator 101 has been positioned within the patient 190, the signal delivery parameters provided by the pulse generator 101 can still be updated remotely via a wireless physician's programmer (e.g., a physician's remote) 109 and/or a wireless patient programmer 106 (e.g., a patient remote). Generally, the patient 190 has control over fewer parameters than does the practitioner. For example, the capability of the patient programmer 106 may be limited to starting and/or stopping the pulse generator 101, and/or adjusting stimulation amplitude.

Figure 2:
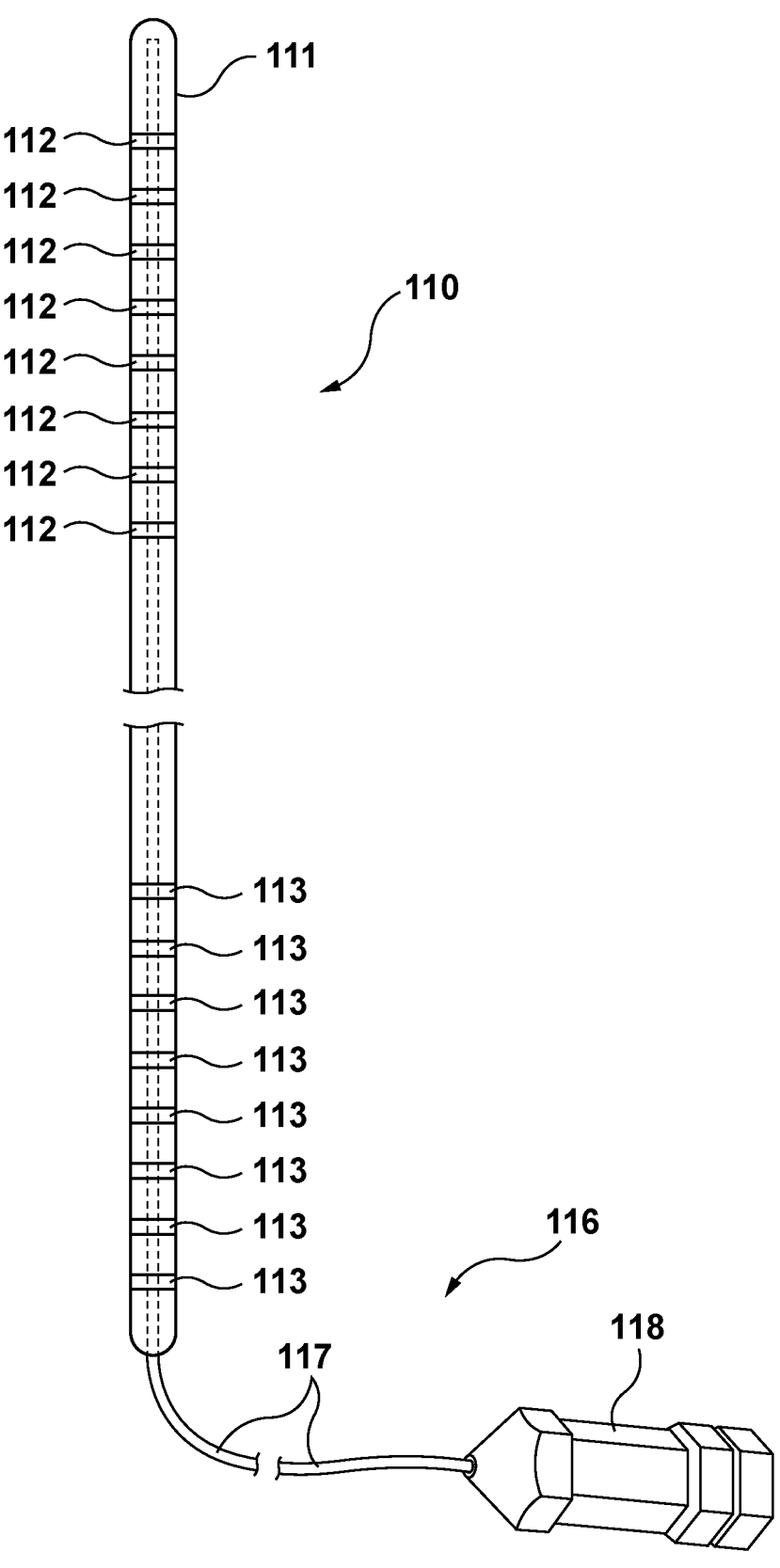
FIG. 2 is a partially schematic illustration of a lead having stimulation contacts and externally positioned connector contacts, suitable for providing stimulation in accordance with representative methods of present disclosure.

FIG. 2 is a partially schematic illustration of a representative signal delivery device 110 that includes a lead 111 having a plurality of stimulation contacts 112 toward the distal end portion that are implanted within the patient. The lead 111 includes internal wires that extend between the stimulation contacts 112 at a distal end portion and portion and connection contacts 113 positioned at the proximal end portion. During the trial period, the connection contacts 113 extend outside the patient's body and are connected to an external stimulator. After the trial period is complete, the connection contacts 113 are connected to the implanted pulse generator 101 (FIG. 1). During implantation, a stylet 116 or other delivery device is temporarily connected to the lead 111 to support the lead 111 as it is positioned within the patient. Accordingly, the stylet 116 can include a shaft 117 and a handle 118. The shaft 117 is generally flexible, but more rigid than the lead 111 to allow the practitioner to insert the lead 111 and control its position during implantation.

Embodiments hereof describe an external neurostimulator having a housing that is configured to directly receive the proximal portions of one or more leads 111, without any connectors and/or cables. Due to the direct connection or attachment between the external neurostimulator and lead(s), the cable assembly 120 shown in FIG. 1 is eliminated, thereby reducing the size and number of system components that must be managed by the patient during the post-operative period. Further, the external neurostimulator is configured to be coupled directly to a patient's skin, preferably at a location adjacent to the treatment site, and thus the system is less awkward and/or cumbersome for the patient during the post-operative trial period.

Figures 3, 4:
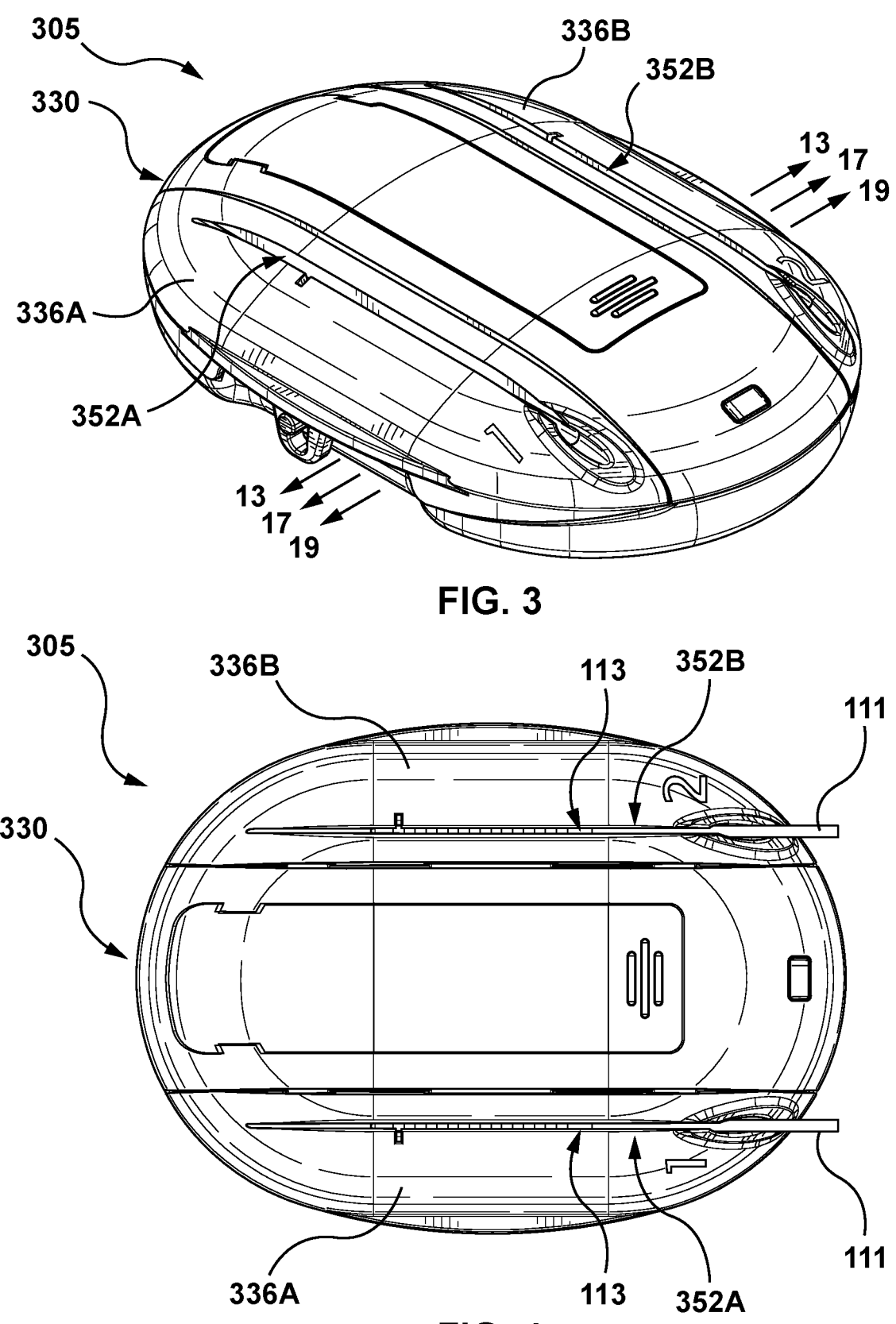
FIG. 3 is a perspective view of an external neurostimulator according to an embodiment of the disclosure.
FIG. 4 is another perspective view of the external neurostimulator of FIG. 3, wherein a pair of leads is shown releasably coupled to the external neurostimulator.
Figure 5:
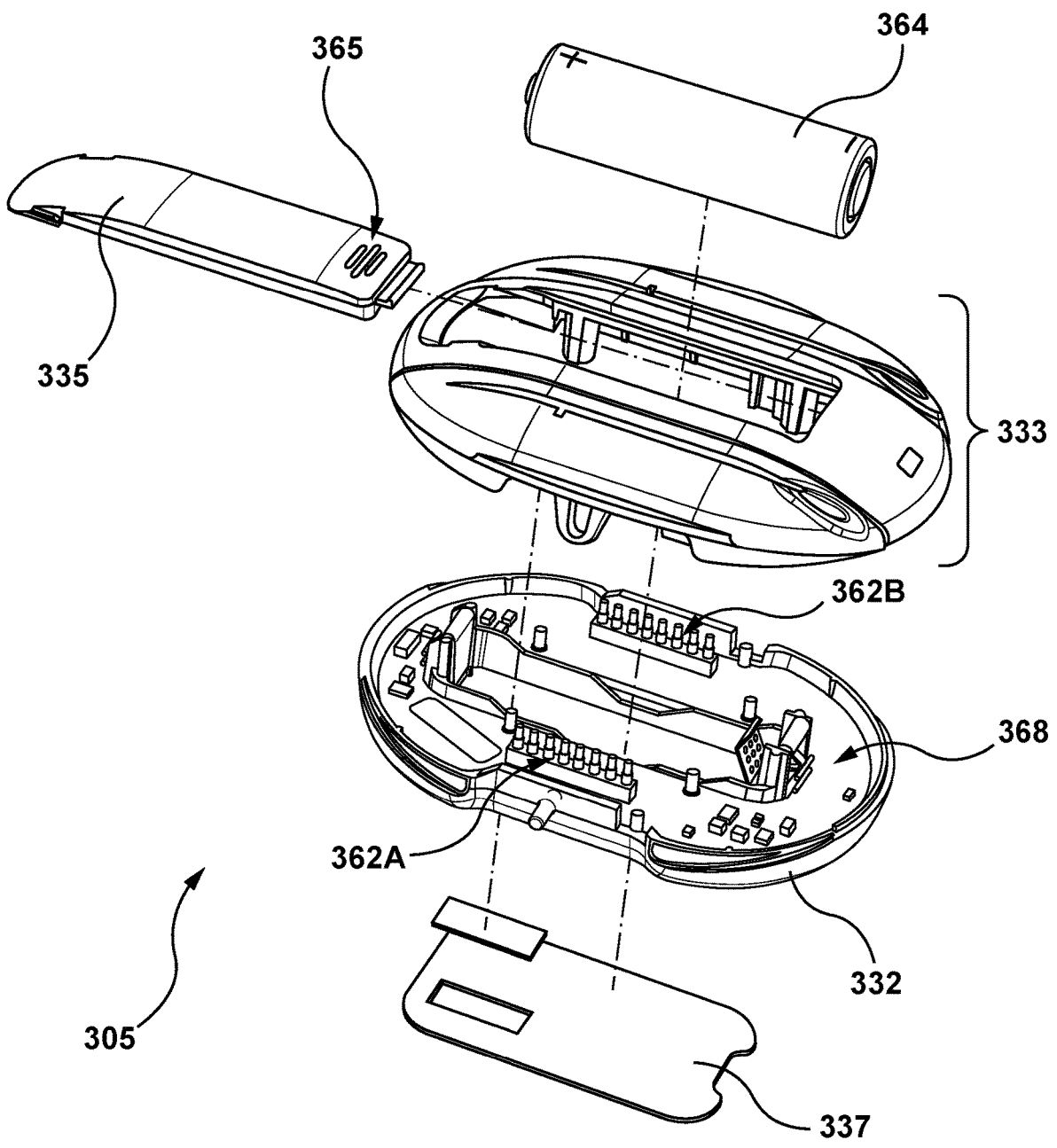
FIG. 5 is an exploded view of the external neurostimulator of FIG. 3.

More particularly, as shown in FIGS. 3-19, an external neurostimulator 305 includes a housing 330, a power source 364 disposed within the housing 330, a signal generator or pulse generator 368 disposed within the housing 330 and electrically coupled to the power source 364, and a first series of spring-loaded pins 362A and a second series of spring-loaded pins 362B electrically coupled to the pulse generator 368. As will described in more detail herein, the housing 330 includes two side doors 336A, 336B, each of which include a channel or slot 352A, 352B, respectively, configured to receive a proximal end portion (having connection contacts 113) of the lead 111 therein. The first and second series of spring-loaded pins 362A, 362B are positioned to releasably, electrically contact the connection contacts 113 of the lead 111 when the lead 111 is positioned within the respective channel 352A, 352B. FIG. 3 illustrates a perspective view of the external neurostimulator 305 without leads 111 coupled thereto, while FIG. 4 illustrates the external neurostimulator 305 with proximal end portions of a pair of leads 111 disposed within the channels 352A, 352B. FIG. 5 illustrates an exploded view of the external neurostimulator 305. As shown in FIG. 5, the external neurostimulator 305 may include a label 337 disposed within or on the housing 330 for identification purposes.

Figure 6:
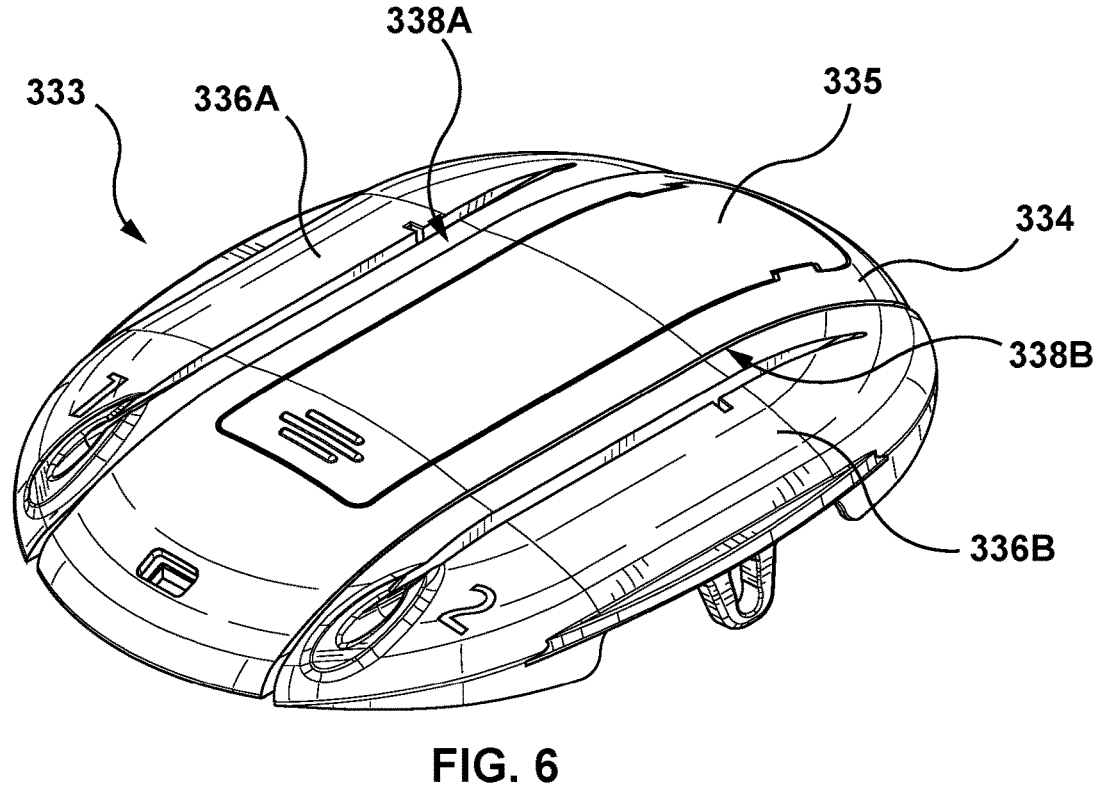
FIG. 6 is a perspective view of a top housing of the external neurostimulator of FIG. 3, wherein the top housing is removed from the external neurostimulator for purposes of illustration only.
Figure 7:
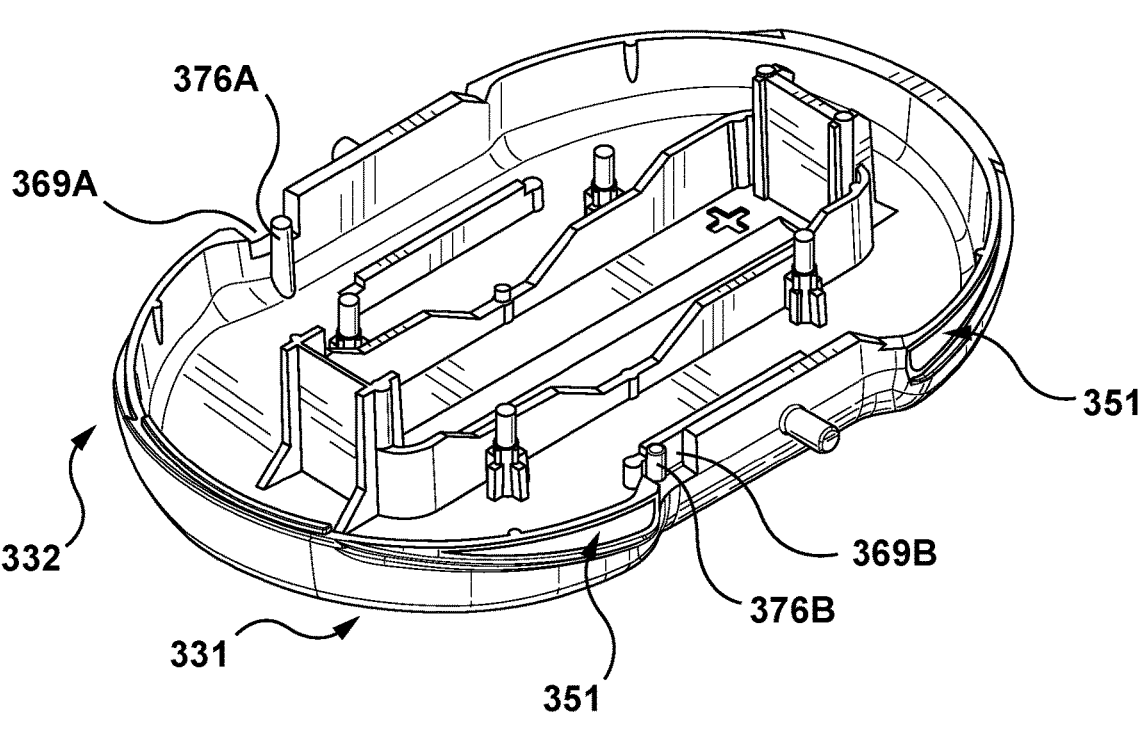
FIG. 7 is a perspective view of a base housing of the external neurostimulator of FIG. 3, wherein the base housing is removed from the external neurostimulator for purposes of illustration only.
Figure 8:
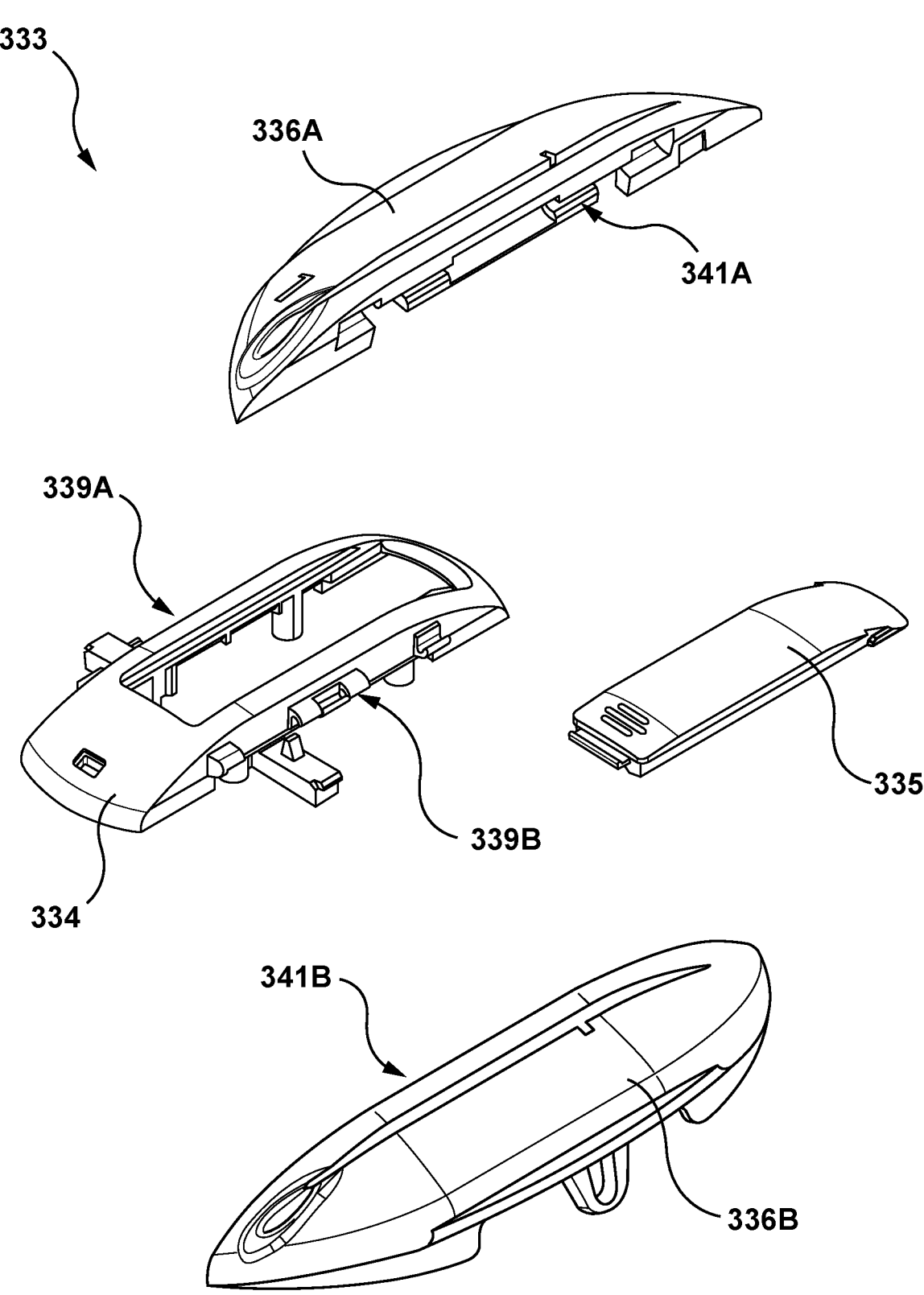
FIG. 8 is an exploded view of the top housing of FIG. 6, wherein the top housing is removed from the external neurostimulator for purposes of illustration only.

Referring to FIGS. 6-8, the housing 330 includes a base housing 332 and a top housing 333 that attach to each other to form or define an enclosed volume. FIGS. 6 and 8 illustrate a perspective and an exploded view, respectively, of the top housing 333 while FIG. 7 illustrates a perspective view of the base housing 332. The bulk of the housing 330 can be formed from ABS or another suitable biocompatible plastic or other material. The base housing 332 includes a bottom surface 331 which is configured to contact and be attached directly to a patient's skin. In addition, the base housing 332 includes one or more recessed outer surface 351 that are brightly colored and function to alert the practitioner that the side doors 336A, 336B are in the partially-opened or unlocked configurations, as will be described in more detail herein with respect to FIGS. 10A and 10B. To increase patient comfort when attached to the patient's skin, a perimeter 329 of the base housing 332 is generally oval shaped and curved (as best shown in FIGS. 9B and 10B). In addition, the top surface of the top housing 333 is also curved such that the external neurostimulator 305 has a curved profile, with the thickest portion thereof in the center of the housing 330 and the edges thereof tapering to a thinner profile around the perimeter. Further, the housing 330 is a relatively thin, small component that is not bulky and thus relatively more comfortable for the patient to wear during the trial period. In an embodiment, the housing 330 has a height between 18 mm and 22 mm, a width between 6 cm and 6.5 cm, and a length between 8 cm and 9 cm.

The top housing 333 includes a central portion 334 that includes a removable battery cover 335, a first side door 336A hingedly coupled to a first side of the central portion 334, and a second side door 336B hingedly coupled to a second or opposing side of the central portion 334. Each of the first and second side doors 336A, 336B is pivotably connected to the central portion 334 of the top housing 333 via a hinged connection 338A, 338B. The hinged connection 338A includes a series of pin apertures 339A on a first side of the central portion 334 of the top housing 333 that collectively slidably receive a corresponding hinge pin 340A. The hinge pin 340A also passes through a series of pin apertures 341A on the first side door 336A. The hinge pin 340A has a snap fit engagement with the pin apertures 341A on the first side door 336A, and the pin apertures 341A are compliant to permit pivoting action with lateral movement of the first side door 336A during opening and closing thereof. The apertures 339A, 341A may be formed via semi-circular wall elements to simplify the manufacturing thereof. Similarly, the hinged connection 338B includes a series of pin apertures 339B on a second side of the central portion 334 of the top housing 333 that collectively slidably receive a corresponding hinge pin 340B (see FIG. 16 in which the second side door 336B is shown in phantom). The hinge pin 340B also passes through a series of pin apertures 341B on the first side door 336B. The hinge pin 340B has a snap fit engagement with the pin apertures 341B on the second side door 336B, and the pin apertures 341B are compliant to permit pivoting action with lateral movement of the second side door 336B during opening and closing thereof. The apertures 339B, 341B may be formed via semi-circular wall elements to simplify the manufacturing thereof. Accordingly, each of the first and second side doors 336A, 336B can be pivoted relative to the central portion 334 of the top housing 333 (and relative to the base housing 332) between a closed or locked configuration and a partially-opened or unlocked configuration, which will be described in more detail herein with respect to FIGS. 9A-10B.

Figure 11:
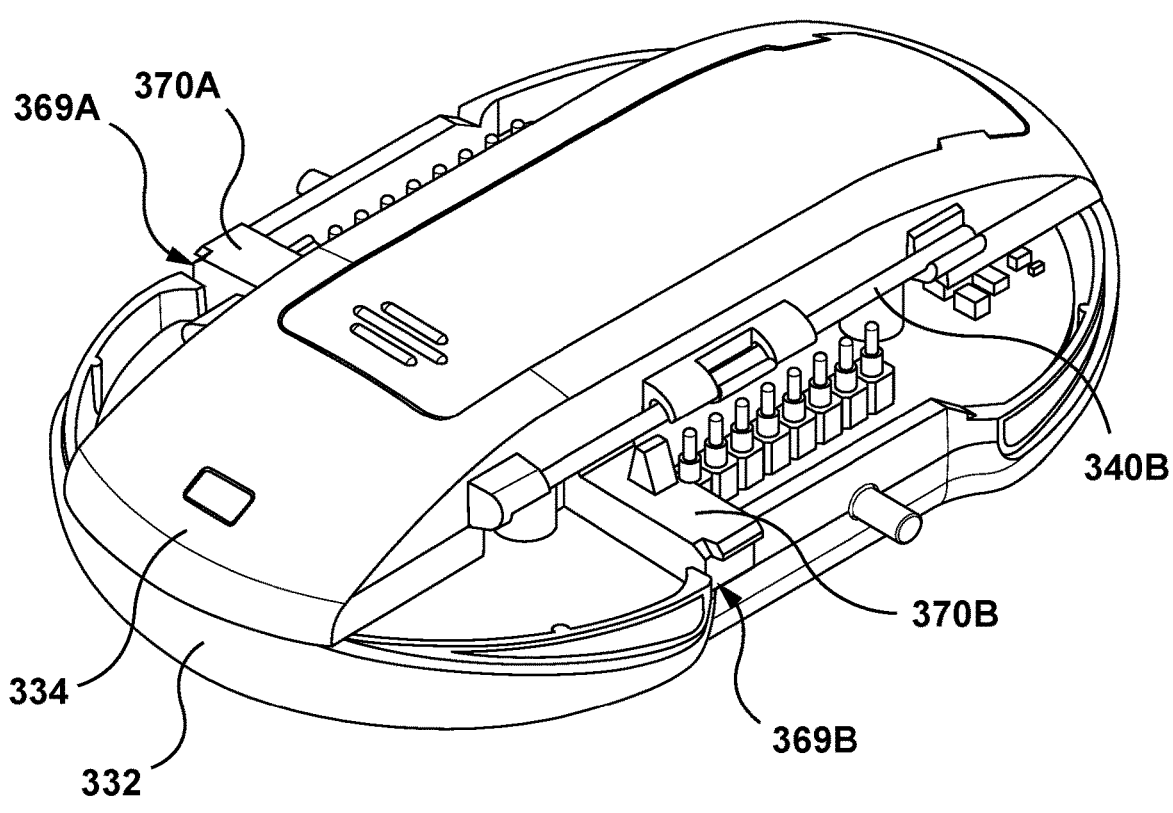
FIG. 11 is a perspective view of the external neurostimulator of FIG. 3, wherein a first side door and a second side door are omitted for sake of illustration only.
Figure 12:
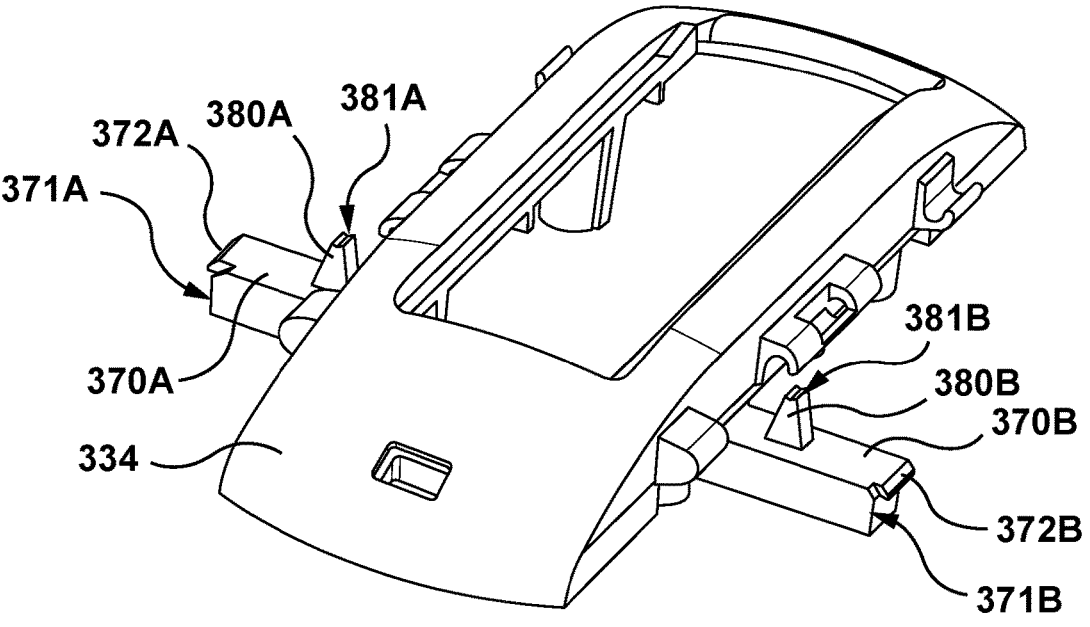
FIG. 12 is a perspective view of a central portion of the top housing of the external neurostimulator of FIG. 3, wherein the central portion is shown removed from the external neurostimulator for sake of illustration only.

More particularly, each of the first side door 336A and the second side door 336B includes a locking mechanism to lock the side door in the closed configuration. When each of the side doors 336A, 336B are in the closed configuration, they are necessarily locked. Conversely, when each of the side doors 336A, 336B are not in the closed configuration, they are necessarily unlocked and in a partially-open configuration. As best shown on FIGS. 11 and 12, the central portion 334 of the top housing 333 includes a first tab 370A and a second tab 370B. FIG. 11 is a perspective view of the external neurostimulator 305 with the first and second side doors 336A, 336B omitted, while FIG. 12 is a perspective view of the central portion 334 of the top housing 333 shown removed from the external neurostimulator 305 for sake of illustration only. The first and second tabs 370A, 370B extend outwardly in opposing directions and are received within corresponding slots or side wall openings 369A, 369B formed in the base housing 332. The first and second tabs 370A, 370B include a hook 372A, 372B, respectively, formed on outermost end 371A, 371B thereof.

Figure 13:
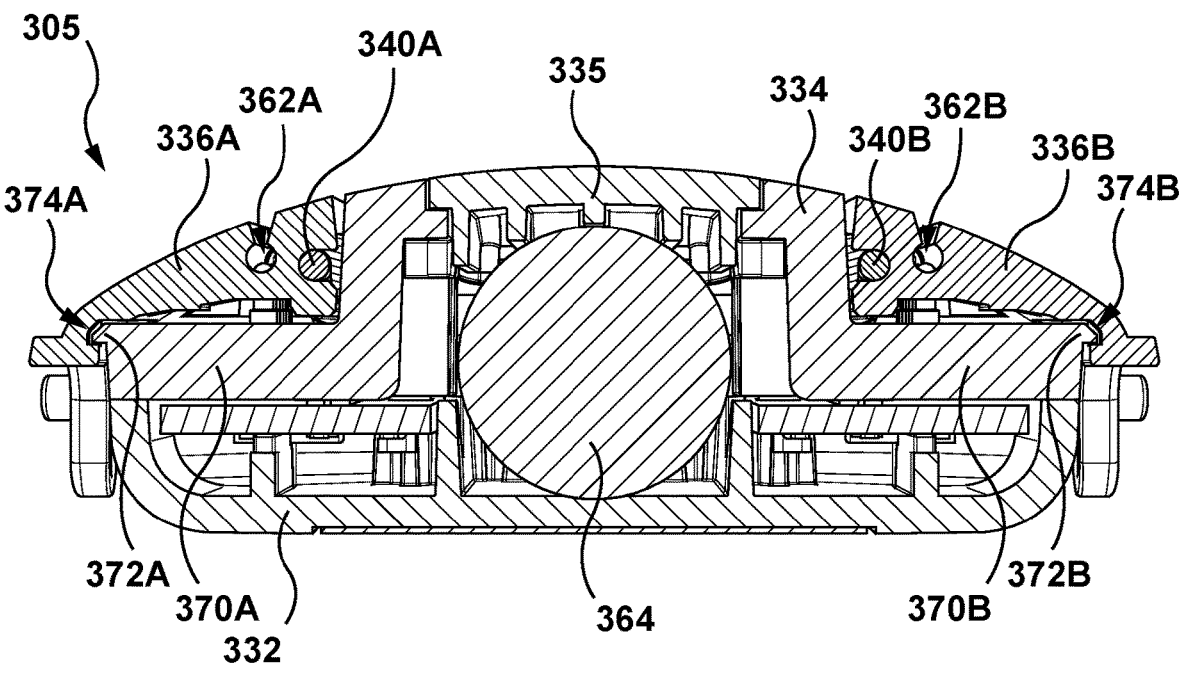
FIG. 13 is a sectional view of the external neurostimulator of FIG. 3, taken along line 13-13 of FIG. 3.
Figure 14:
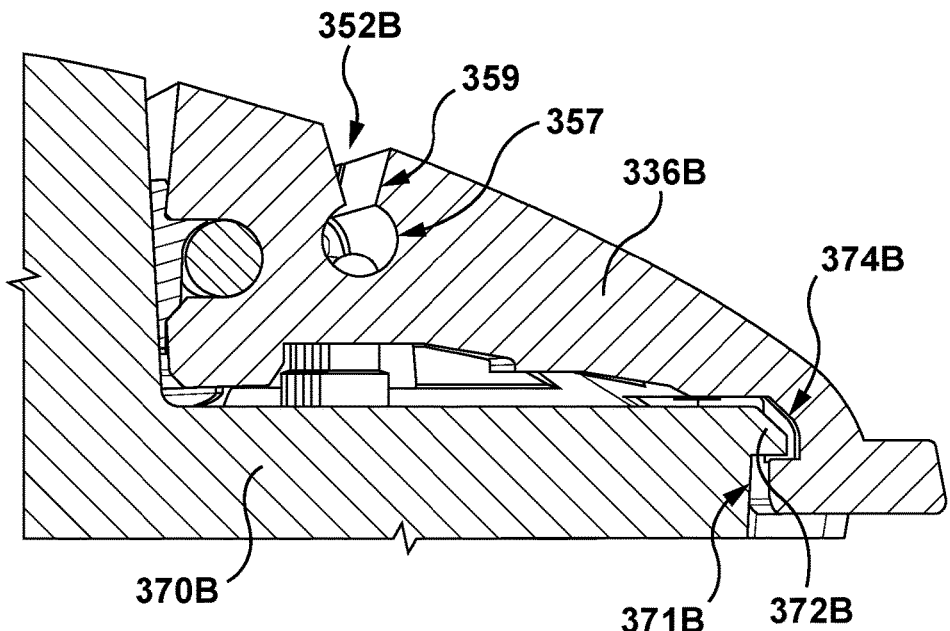
FIG. 14 is an enlarged view of a portion of FIG. 13.
Figure 15A:
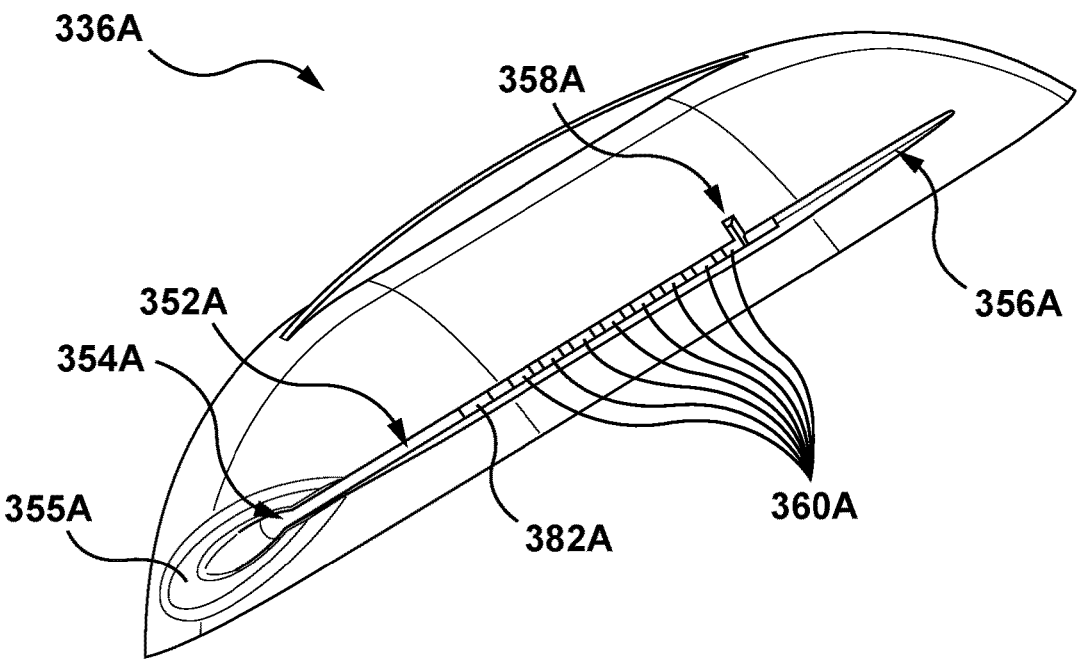
FIG. 15A is a perspective view of the first side door of the external neurostimulator of FIG. 3, wherein the first side door is shown removed from the external neurostimulator for sake of illustration only.
Figure 15B:
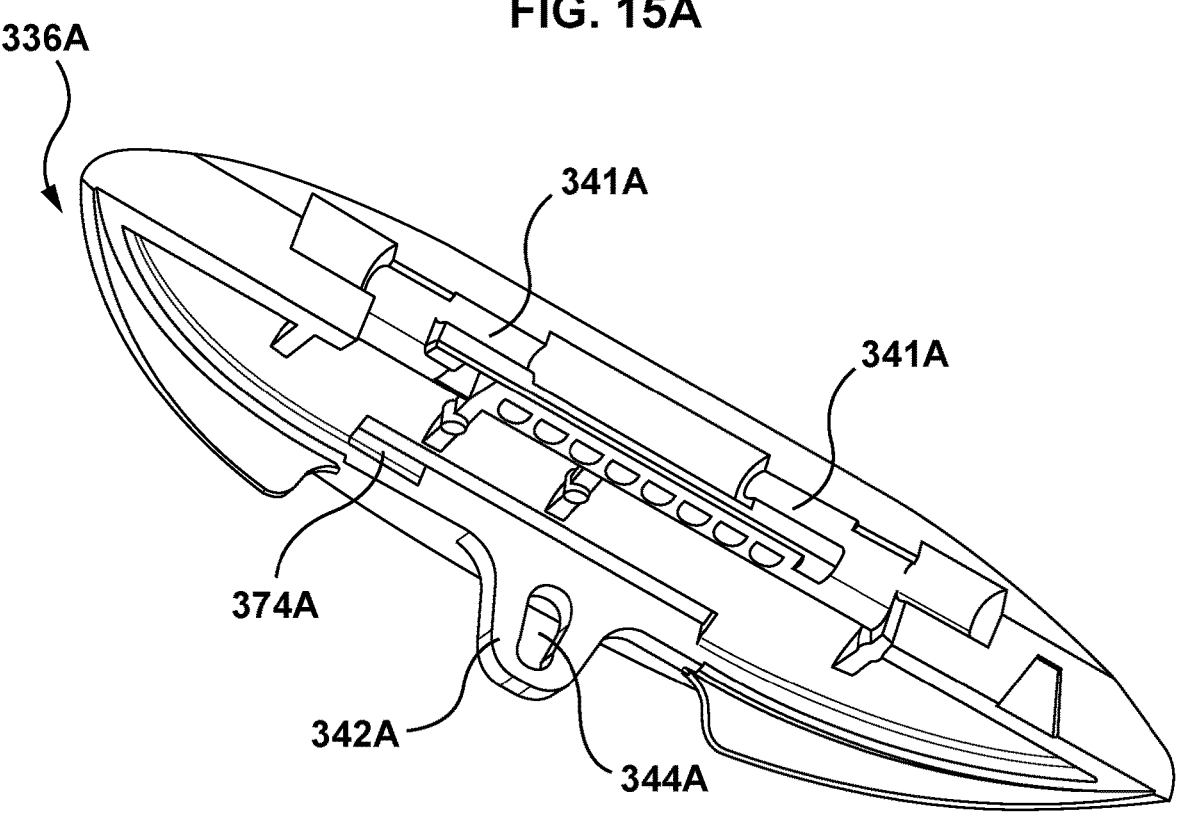
FIG. 15B is another perspective view of the first side door of the external neurostimulator of FIG. 3, wherein the first side door is shown removed from the external neurostimulator for sake of illustration only.
Figure 15E:
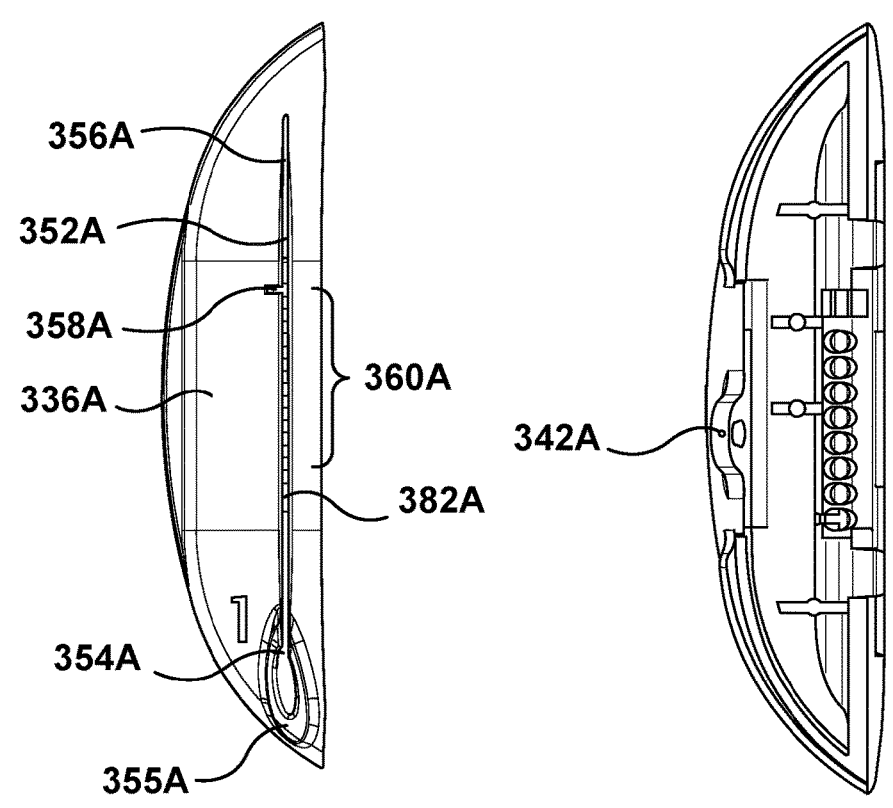
FIG. 15E is a side view of the first side door of the external neurostimulator of FIG. 3, wherein the first side door is shown removed from the external neurostimulator for sake of illustration only.
Figure 15E:
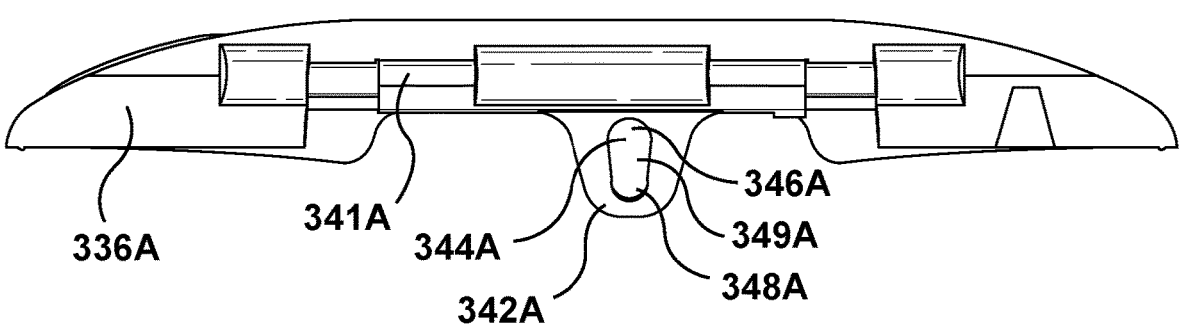

As best shown on the sectional views of FIGS. 13 and 14, in the closed or locked configuration of the first side door 336A, the hook 372A of the first tab 370A is received within a recess 374A formed on an inner surface of the first side door 336A. The hook 372A and the recess 374A have a mating or corresponding engagement that prevents the first side door 336A from opening when the hook 372A is received or disposed within the recess 374A, absent an external force applied thereto which is sufficient to open the first side door 336A to the partially-open configuration. Similarly, in the locked configuration of the second side door 336B, the hook 372B of the second tab 370B is received within a recess 374B formed on an inner surface of the second side door 336B. The hook 372B and the recess 374B have a mating or corresponding engagement that prevents the second side door 336B from opening when the hook 372B is received or disposed within the recess 374B, absent an external force applied thereto which is sufficient to open the second side door 336B to the partially-open configuration.

Figure 17:
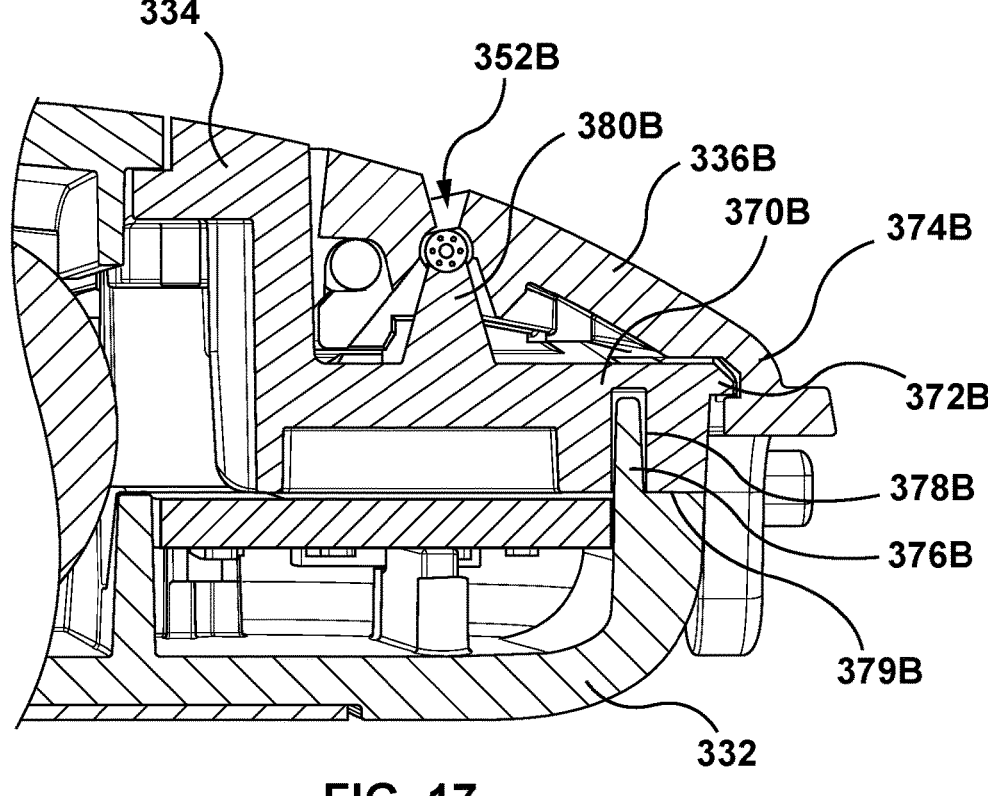
FIG. 17 is a sectional view of a portion of the external neurostimulator of FIG. 3, taken along line 17-17 of FIG. 3.

As best shown on the sectional view of FIG. 17, to further stabilize the first and second side doors 336A, 336B in the locked configurations, the base housing 332 includes a first snap fit feature 376A and a second snap fit feature 376B extending therefrom. Although the first snap fit feature 376A is not shown in FIG. 17, the first snap fit feature 376A is a mirror image of the second snap fit 376B and thus it will be apparent to one of ordinary skill in the art that the first snap fit feature 376A includes the same features as shown and described with respect to the second snap fit feature 376B. The second snap fit feature 376B mates with or is received within a corresponding opening 378B formed on an underside surface 379B of the second tab 370B of the central portion 334. Similarly, the first snap fit feature 376A mates with or is received within a corresponding opening 378A formed on an underside surface 379A of the first tab 370A of the central portion 334. The snap fit features 376A, 376B are disposed adjacent to and below the hooks 372A, 372B, respectively, and reinforce the connection between the hooks 372A, 372B and the recesses 374A, 374B when the side doors 336A, 336B are in their closed or locked configurations.

With reference now to FIGS. 9A-10B, each of the first side door 336A and the second side door 336B includes a latch 342A, 342B that interfaces with a post or stop element 350A, 350B on the base housing 332 to control or limit the pivoting motion of the first and second side doors 336A, 336B. As such, when the first and second side doors 336A, 336B are pivoted relative to the base 332, the first and second side doors 336A, 336B may only be partially opened. Stated another way, pivoting motion of the first and second side doors 336A, 336B is limited such that each side door has a partially-opened configuration rather than a fully open configuration.

Each latch 342A, 342B extends towards the base housing 332 and has an opening 344A, 344B, respectively, formed therethrough. The base housing 332 includes the first post 350A extending outwardly therefrom and the second post 350B extending outwardly therefrom, the first and second posts 350A, 350B being formed on opposing sides of the base housing 332. The latch 342A of the first side door 336A is configured to receive the first post 350A and the latch 342B of the second side door 336B is configured to receive the second post 350B. The opening 344A, 344B of each latch 342A, 342B includes a top circular portion 346A, 346B, respectively, a bottom circular portion 348A, 348B, respectively, and a waisted portion 349A, 349B, respectively, disposed between the top and bottom circular portion. Stated another way, each opening 344A, 344B has opposing ends that are wider than a middle portion thereof, which has pinched or narrowed sides. For example, each opening 344A, 344B may be described as dumbbell or peanut shaped, and can be hourglass-shaped in another embodiment.

Figure 9A:
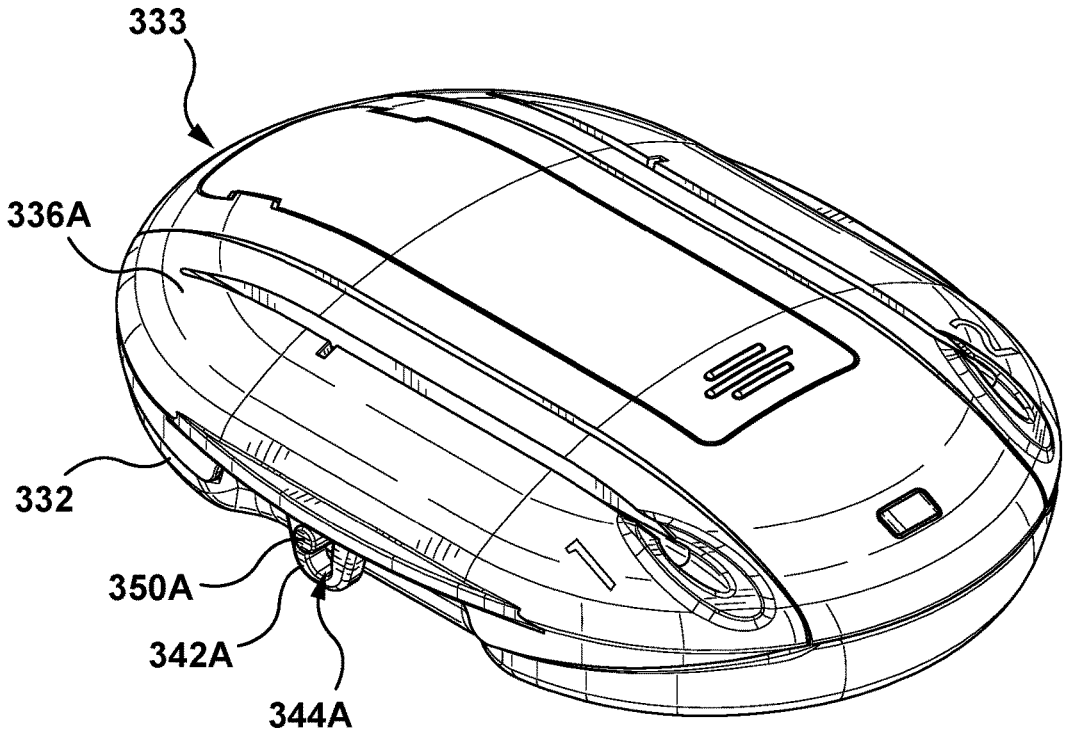
FIG. 9A is a perspective view of the external neurostimulator of FIG. 3, wherein the external neurostimulator is shown in its closed or locked configuration.
Figure 9B:
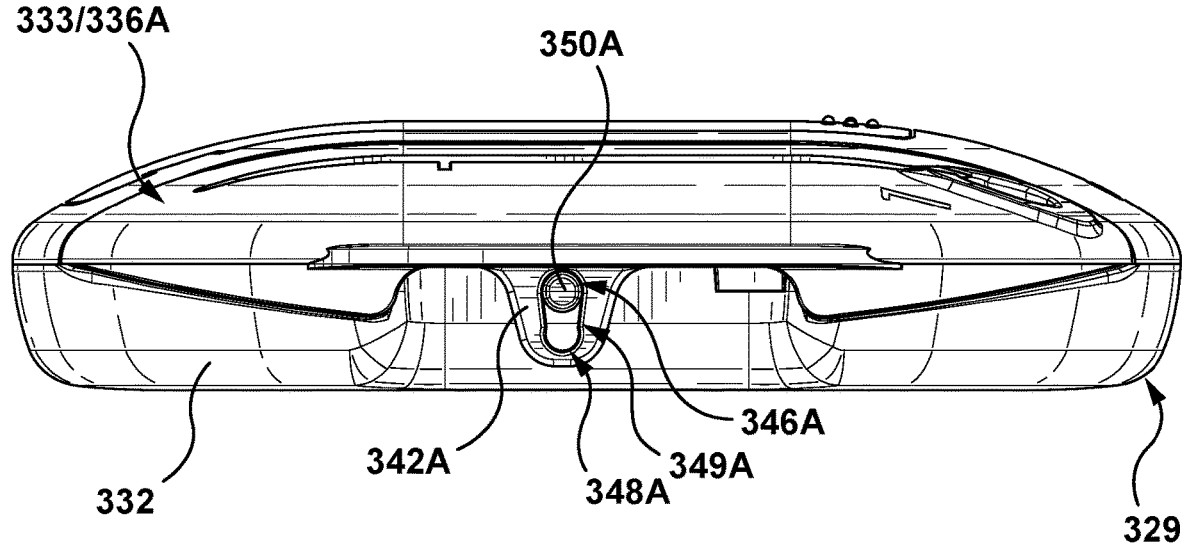
FIG. 9B is a side view of the external neurostimulator of FIG. 3, wherein the external neurostimulator is shown in its closed or locked configuration.
Figures 10A, 10B:
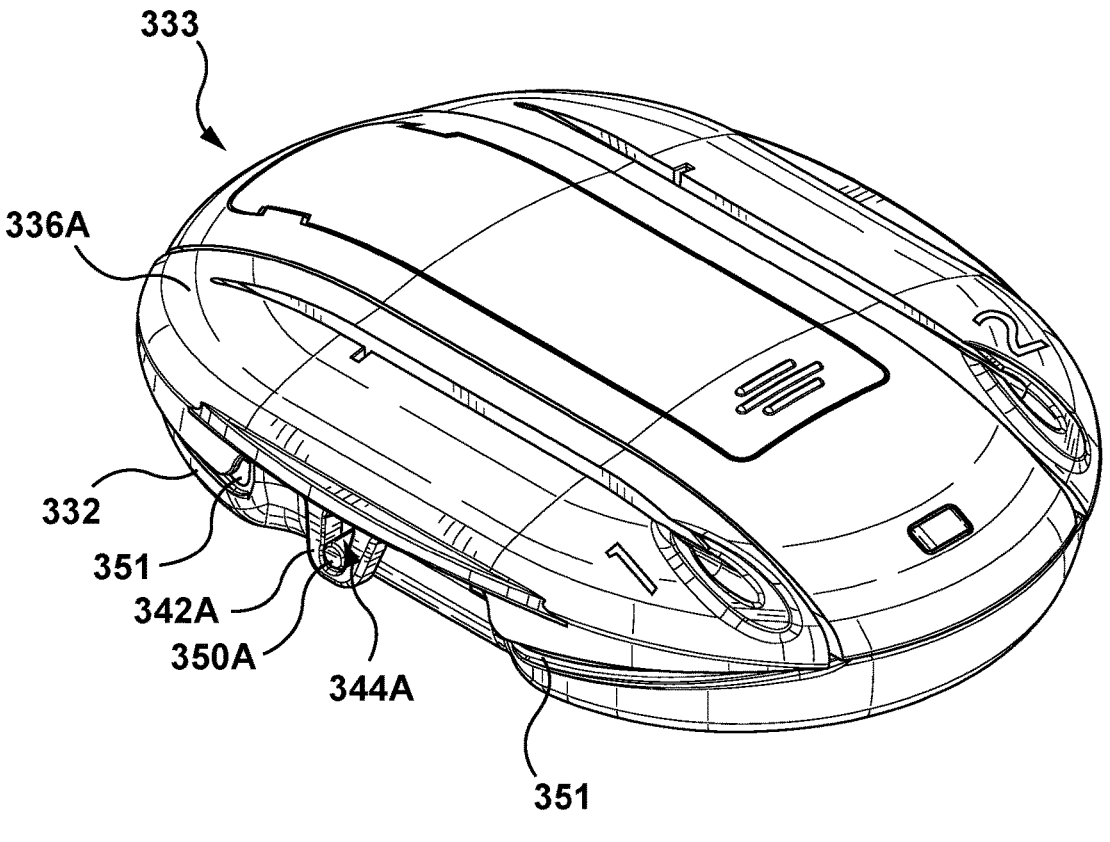
FIG. 10A is a perspective view of the external neurostimulator of FIG. 3, wherein the external neurostimulator is shown in its partially open or unlocked configuration.
FIG. 10B is a side view of the external neurostimulator of FIG. 3, wherein the external neurostimulator is shown in its partially open or unlocked configuration.

FIGS. 9A-10B are partially schematic, isometric views of an embodiment of the external neurostimulator 305 shown in a partially-opened or unlocked configuration and a closed or locked configuration in accordance with an embodiment of the disclosure. FIGS. 9 and 9B illustrates the external neurostimulator 305 in the closed or locked position in which the posts 350A, 350B are in a second location in latches 342A, 342B, respectively. In the closed or locked configuration of the first side door 336A, the first post 350A is disposed in the top circular portion 346A of the opening 344A of the latch 342A of the first side door 336A. Similarly, in the closed or locked configuration of the second side door 336B, the second post 350B is disposed in the top circular portion 346B of the opening 344B of the latch 342B of the second side door 336B. FIGS. 10A and 10B illustrate the external neurostimulator 305 in the partially-opened or unlocked position in which the posts 350A, 350B are in a first location in latches 342A, 342B, respectively. In the partially-open or unlocked configuration of the first side door 336A, the first post 350A is disposed in the bottom circular portion 348A of the opening 344A of the latch 342A of the first side door 336A. Similarly, in the partially-open or unlocked configuration of the second side door 336B, the second post 350B is disposed in the bottom circular portion 348B of the opening 344B of the latch 3432B of the second side door 336B. In addition, as previously introduced, the base housing 332 includes one or more recessed outer surface 351 that are brightly colored and function to alert the practitioner that the side doors 336A, 336B are in the partially-opened or unlocked configurations. The recessed outer surfaces 351 are only visible to the practitioner when the side doors 336A, 336B are in the partially-opened or unlocked configurations, as shown in FIGS. 10A and 10B, and are not visible when the side doors 336A, 336B are in the closed or locked configurations because they are covered by the side doors 336A, 336B, as shown in FIGS. 9A and 9B. The recessed outer surfaces 351 may be an orange, red, or other bright color that is different from the color of the rest of the base housing 332 so that when visible, they function to alert the practitioner that one or both of the side doors 336A, 336B has been inadvertently unlocked.

The location of the posts 350A, 350B relative to the openings 344A, 344B of the latches 342A, 342B change as the first and second side doors 336A, 336B of the external neurostimulator 305 move from the partially-opened or unlocked configuration to the closed or locked position. The change in relative location results from the relative movement of the side doors 336A, 336B and the base housing 332, regardless of which housing component moves relative to the other. Due to the interfacing between the posts 350A, 350B and the latches 342A, 342B, the first and second side doors 336A, 336B are prevented from over-rotating relative to the base portion 332. In a particular embodiment, the openings 344A, 344B of the latch 342A, 342B can be sized to prevent the first and second side doors 336A, 336B from rotating away from the base housing 332 by an angle between 0.5° and 45°, inclusive. In other embodiments, the amount of rotation can be less, for example, between 3° and 15°, inclusive, between 5° and 8°, inclusive, or between 6.5° and 7°, inclusive. The particular angular value can be selected so that the connection contacts of the lead just disengage from the spring-loaded pins 362A, 362B when the external neurostimulator 305 is in the partially-opened or unlocked configuration. Another feature of at least some of the foregoing embodiments is that the angle between the side doors 336A, 336B and the base housing 332 is relatively small when the external neurostimulator 305 is in the partially-opened or unlocked configuration. For example, the angle can be between 0.5° and 45° in a particular embodiment, between 3° and 15° in another particular embodiment, between 5° and 8° in a further particular embodiment, and between 6.5° and 7° in still a further particular embodiment. Accordingly, the amount of hand movement required to secure and/or unsecure each of the first and second side doors 336A, 336B is relatively small, which allows a practitioner to manipulate a side door singlehandedly and also decreases the likelihood that the practitioner will fumble with the external neurostimulator 305.

Due to the dumbbell or peanut shape of the openings 344A, 344B, the practitioner receives tactile feedback when the posts 350A, 350B move between the top circular portions 346A, 346B and the bottom circular portions 348A, 348B of the openings 344A, 344B. More particularly, when the posts 350A, 350B move or pass over the waisted portions 349A, 349B, the practitioner feels a click that indicates that the posts 350A, 350B are moving positions within the openings 344A, 344B. The posts 350A, 350B function as a hard stop during opening of the side doors 336A, 336B, respectively.

With additional reference to FIGS. 15A-15E, the side doors 336A, 336B will be described in more detail. FIGS. 15A-15E illustrate various views of the first side door 336A. Although the second side door 336B is not shown, the second side door 336B is a mirror image of the first side door 336A and thus it will be apparent to one of ordinary skill in the art that the second side door 336B includes the same features as shown and described with respect to the first side door 336A. As stated above, each of the first side door 336A and the second side door 336B include the channel 352A, 352B, respectively, formed thereon that is configured to directly releasably receive a proximal end portion of the lead 111. The proximal end portion of the lead 111 includes the connection contacts 113 thereon. Each channel 352A, 352B is elongated along its longitudinal axis. Each channel 352A, 352B includes a first end 354A, 354B, respectively, and a second end 356A, 356B, respectively, opposing the first end 354A, 354B. Each first end 354A, 354B is configured as a lead insertion entry point. Each first end 354A, 354B includes a horseshoe-shaped surface protrusion 355A, 355B formed adjacent thereto to provide a visual indication of the lead insertion entry point and further to facilitate sliding a lead into the channel 352A, 352B. Each horseshoe-shaped surface protrusion 355A, 355B is a raised surface element formed on the first and second side doors 336A, 336B, respectively. A lead can be introduced into the channel 352A, 352B by sliding it axially into and along the channel 352A, 352B. As a result, the lead can be moved into the channel 352A, 352B easily, with low frictional resistance, and with a reduced likelihood for dislodging or otherwise moving the lead relative to the patient. When the practitioner does engage the connection contacts of the lead with the spring-loaded pins of the external neurostimulator 305 by closing or locking the side doors 336A, 336B, the practitioner can do so with only one hand, allowing the practitioner to hold the lead in place relative to the patient with the other hand.

Each channel 352A, 352B also includes a notch 358A, 358B formed between the first end 354A, 354B, respectively, and the second end 356A, 356B, respectively. Each notch 358A, 358B extends outwardly from the longitudinal axis of the channel 352A, 352B, respectively, and is configured to be a lead depth indicator point. Each notch 358A, 358B functions as a depth indicator to provide the practitioner with visual confirmation that the lead is properly inserted into the channel 352A, 352B, respectively.

Each channel 352A, 352B is configured to receive a lead or other signal delivery device, and an associated stylet. More particularly, as best shown on FIG. 14, each channel 352A, 352B has a cross-section that includes a circular portion 357 configured to receive the lead 111 or other signal delivery element and a trapezoidal portion 359 configured to receive a stylet. The circular portion 357 is sized and configured to receive the lead 111, while the trapezoidal portion 359 has a variable width and is sized and configured to receive the stylet shaft. In addition, due to the configuration of each channel 352A, 352B, a practitioner is able to see or visualize placement of the lead therein.

Figure 16:
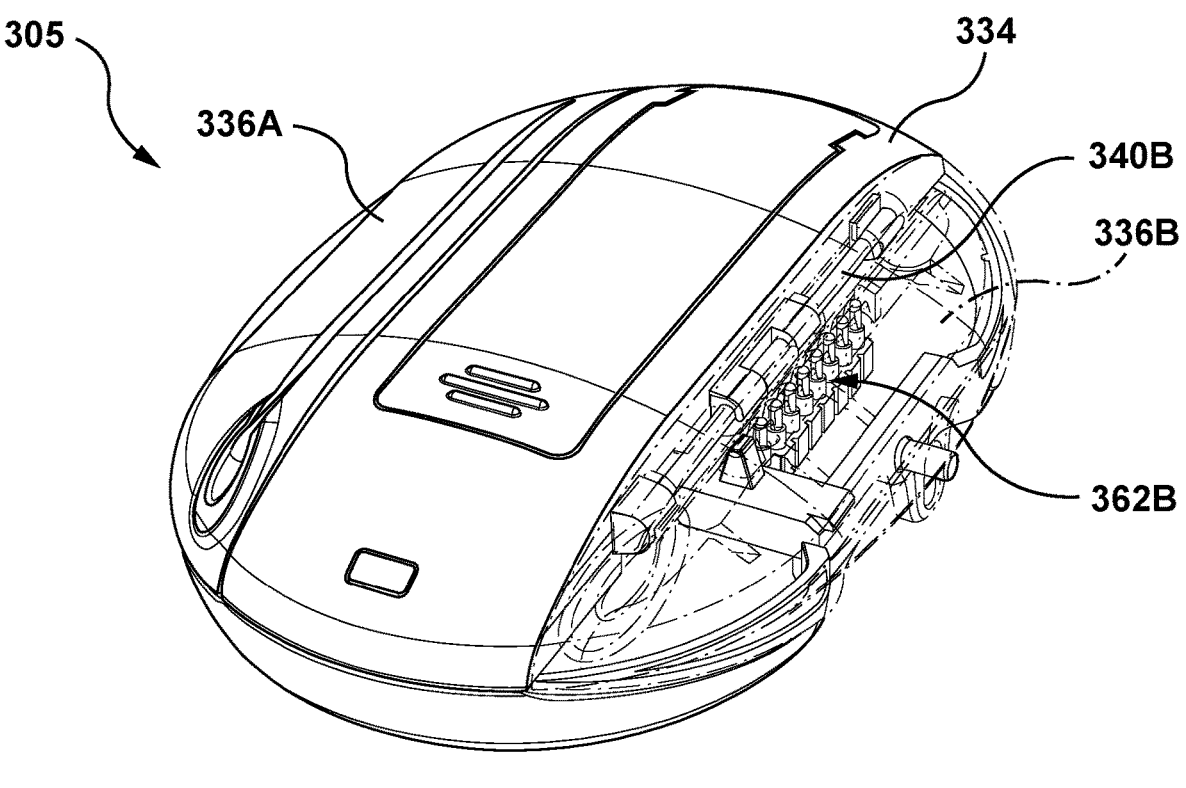
FIG. 16 is a perspective view of the external neurostimulator of FIG. 3, wherein a second side door is shown in phantom for sake of illustration only.

Each channel 352A, 352B includes a series of longitudinally spaced-apart openings 360A, 360B formed on the first side door 336A and the second side door 336B, respectively. With reference to FIG. 16, which illustrates the external neurostimulator with the second side door 336B in phantom for sake of illustration, the first series of spring-loaded pins 362A extend through the series of longitudinally spaced-apart openings 360A of the channel 352A on the first side door 336A and the second series of spring-loaded pins 362B extend through the series of longitudinally spaced-apart openings 360B of the channel 352B on the second side door 336B. Each spring-loaded pin of the first series and the second series of spring-loaded pins 362A, 362B project upwardly from the base housing 332 toward the top housing 333 so as to releasably engage with the lead 111 placed in the channel 352A, 352B of the respective side door 336A, 336B. Each spring-loaded pin of the first series and the second series of spring-loaded pins 362A, 362B is configured to contact a connection contact 113 of the proximal portion of the lead 111. Stated another way, the number of spring-loaded pins in each of the first series and the second series of spring-loaded pins 362A, 362B and the number of openings on each of the series of longitudinally spaced-apart openings 360A, 360B are equal to the number of connection contacts 113 on the lead 111. A single spring-loaded pin 362A, 362B extends through a single opening 360A, 360B to contact and electrically connect to a single connection contact 113 on the lead 111. Thus, although the external neurostimulator is shown with eight openings 360A to receive the eight connection contacts 113 on the lead 111, the number of openings may vary depending upon the lead to be received.

As best shown on FIG. 12 and the sectional view of FIG. 17, to ensure a strong connection between the spring-loaded pins 362A, 362B and the connection contacts 113 of the lead 111, a boss 380A, 380B is formed on each of the first tab 370A and the second tab 370B of the central portion 334 of the top housing 333. Each boss 380A, 380B is configured to apply pressure onto the proximal end portion of the lead 111 when the side door 336A, 336B, respectively, is in the closed or locked configuration. Each channel 352A, 352B includes an opening 382A, 382B (shown on FIG. 15A and FIG. 15C) formed on the first side door 336A and the second side door 336B, respectively. The boss 380A extends through the opening 382A of the channel 352A on the first side door 336A and the boss 380B extends through the opening 382B of the channel 352B on the second side door 336B. Each boss 380A, 380B projects upwardly from the first or second tab 370A, 370B, respectively, towards the side door 336A, 336B, respectively, so as to releasably engage with the lead 111 placed in the channel 352A, 352B of the respective side door 336A, 336B. A top surface 381A, 381B of each boss 380A, 380B is curved so as to conform to the lead 111 when in contact therewith.

Figure 18:
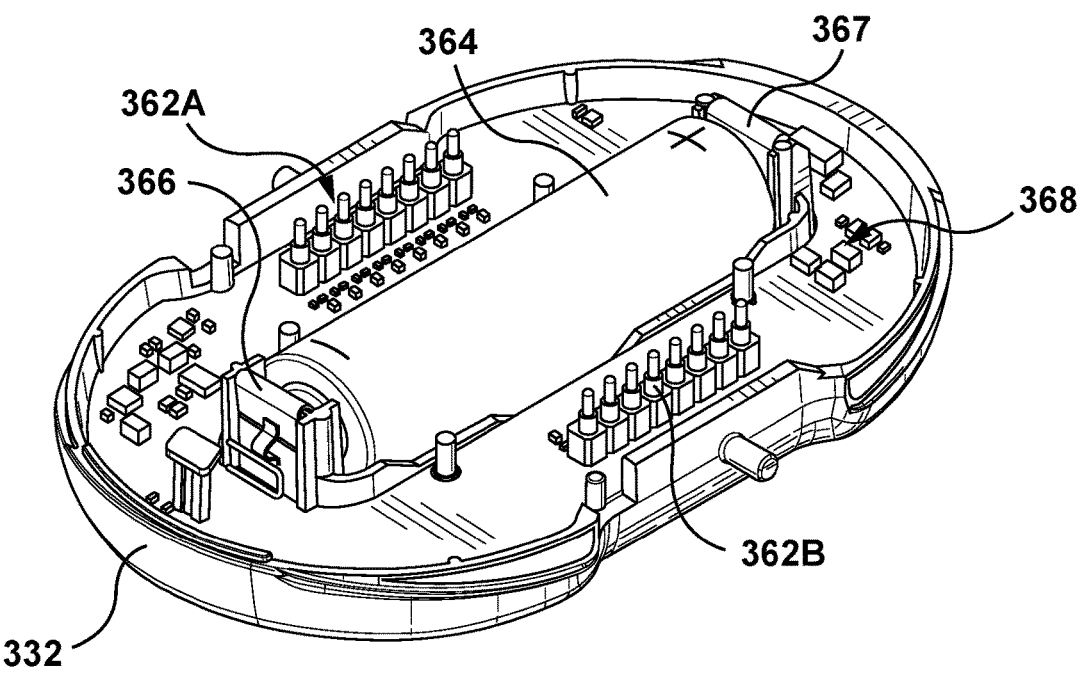
FIG. 18 is a perspective view of the external neurostimulator of FIG. 3, wherein the top housing is omitted from the external neurostimulator for sake of illustration only.
Figure 19:
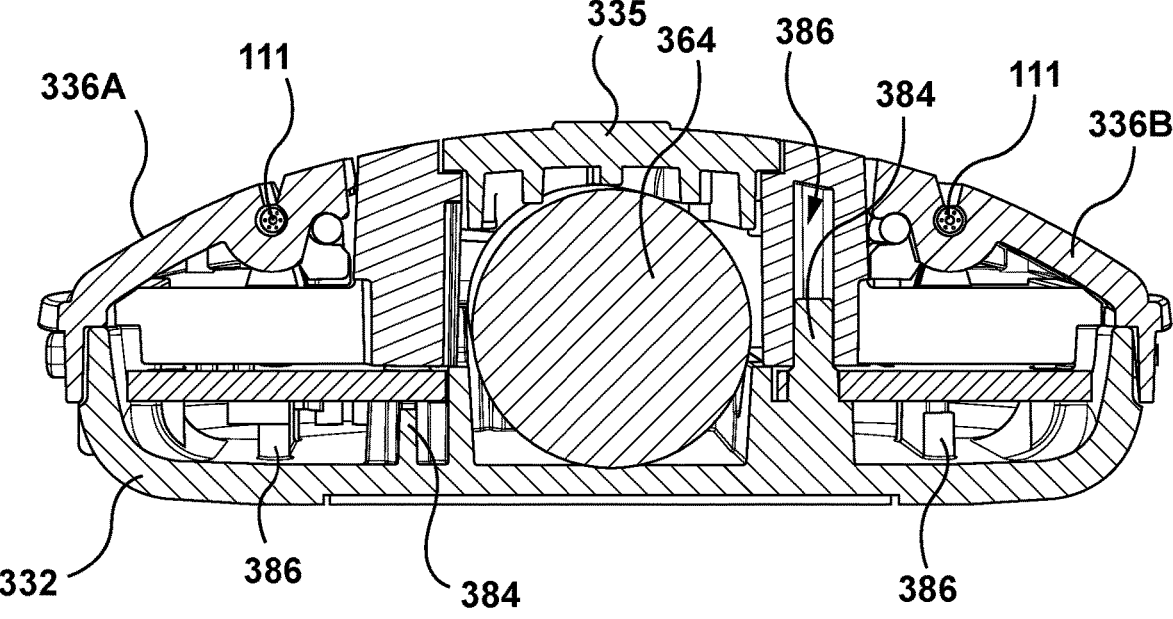
FIG. 19 is a sectional view of the external neurostimulator of FIG. 3, taken along line 19-19 of FIG. 3.

Turning now to FIGS. 18 and 19, assembly of the external neurostimulator 305 will be described in more detail. The power source 364 and the signal generator or pulse generator 368 is disposed within the housing 330 as shown in FIG. 18, which illustrates the external neurostimulator 305 with the top housing 333 omitted for sake of illustration. The power source 364 may be, for example, a commercially available, high energy lithium battery. In an embodiment, the signal generator or pulse generator 368 may include a printed circuit board assembly. The signal generator or pulse generator 368 is electrically coupled to the power source 364 via a first battery clip 366, which receives the negative end of the power source 364, and a second battery clip 367, which receives the positive end of the power source 364. The first series of spring-loaded pins 362A and the second series of spring-loaded pins 362B are also electrically coupled to the pulse generator 368. The power source 364 is removable and replaceable, and is easily accessed via the removable battery cover 335 of the top housing 333. The removable battery cover 335 may include a plurality of ridges 365 (shown on FIG. 5) formed thereon to assist the practitioner in gripping the removable battery cover 335 when removing or repositioning the battery cover.

As shown in the sectional view of FIG. 19, the base housing 332 includes a plurality of supports 386 extending upwardly towards the top housing 333. The supports 386 are positioned under the signal generator or pulse generator 368 to prevent flexing or bending thereof. The base housing 332 is attached to the top housing 333 via one or more bosses or press fit features 384. The base housing 332 includes the bosses 384 extending upwardly towards the top housing 333, and the bosses 384 press fit or are disposed within a corresponding socket or opening 386 formed on an underside surface of the central portion 334 of the top housing 333. The bosses 384 also function to align or position the signal generator or pulse generator 368 within the housing 330.

Figure 20:
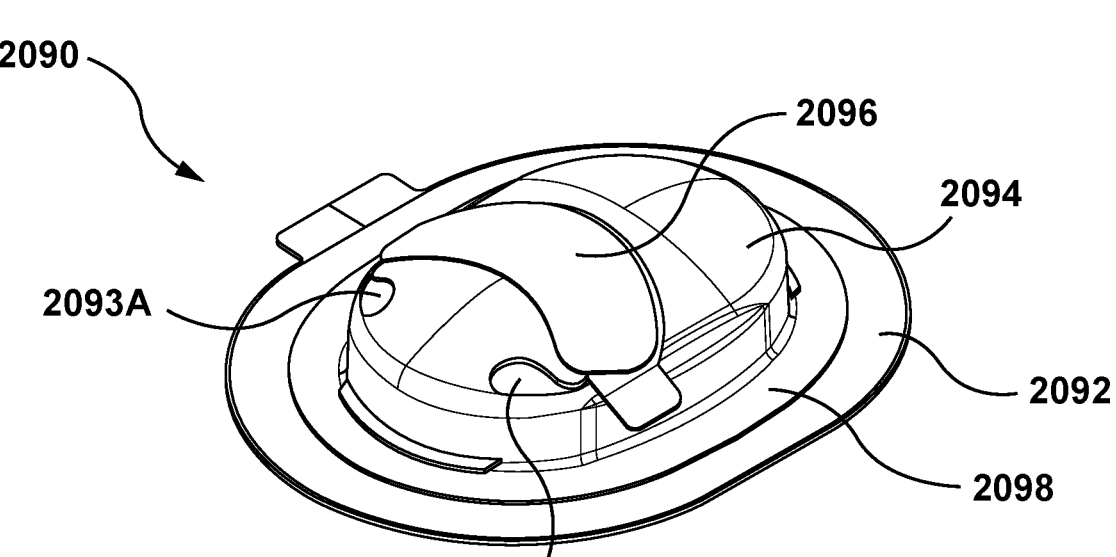
FIG. 20 is a perspective view of a pouch configured to receive the external neurostimulator of FIG. 3 and configured to be attached to a patient's skin.
Figure 21:
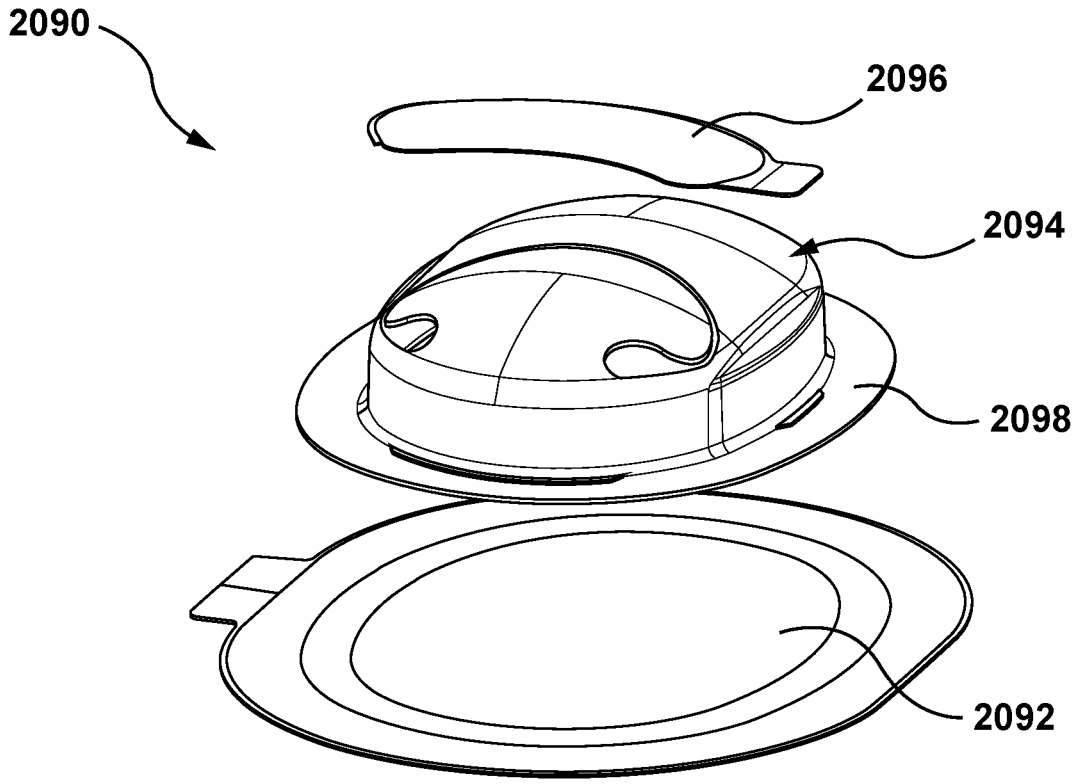
FIG. 21 is an exploded view of the pouch of FIG. 20.
Figure 22:
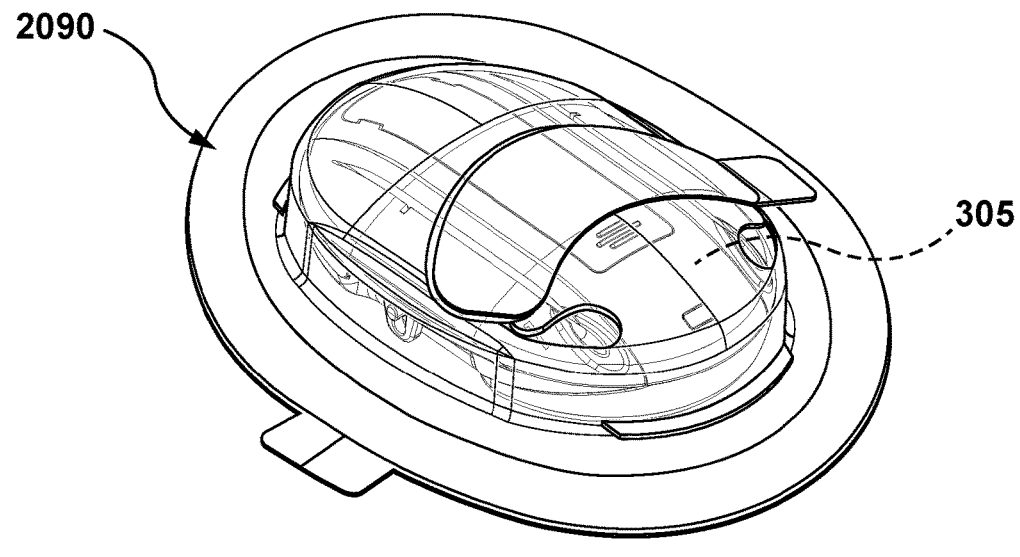
FIG. 22 is a perspective view of the pouch of FIG. 20 with the external neurostimulator of FIG. 3 disposed therein.
Figure 23:
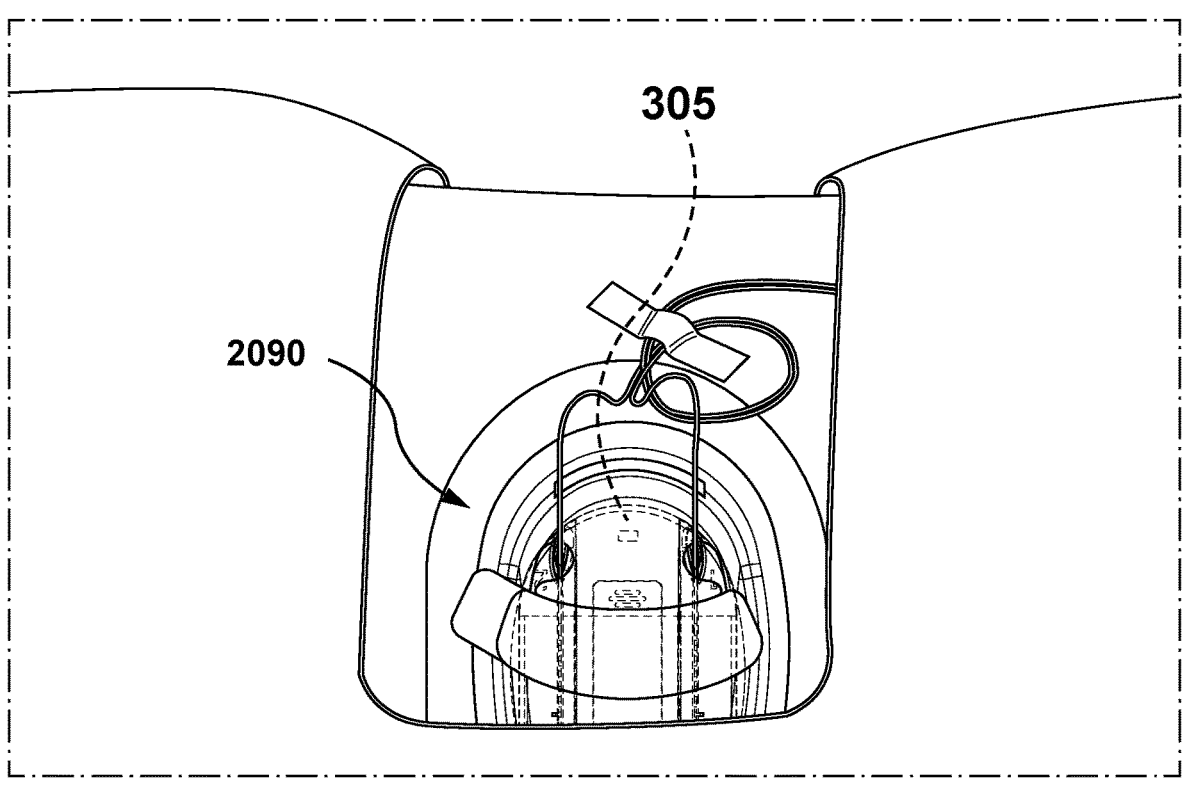
FIG. 23 illustrates the pouch of FIG. 20 with the external neurostimulator of FIG. 3 disposed therein attached to a patient's skin.

The external neurostimulator is particularly configured to be attached directly to a patient's skin as described above, or may be disposed within a pouch that is attached directly to a patient's skin. More particularly, FIG. 20 and FIG. 21 are a perspective view and an exploded view, respectively, of a pouch 2090 that is configured to receive the external neurostimulator 305 and is configured to be attached to a patient's skin. FIG. 22 is a perspective view of the pouch 2090 with the external neurostimulator 305 disposed therein, and FIG. 23 illustrates the assembly of the pouch 2090 and the external neurostimulator 305 attached to a patient. As best shown in the exploded view of FIG. 21, the pouch 2090 includes a base or substrate 2092 and a cover 2094. The cover 2094 is configured to snugly extend over the external neurostimulator 305 so that movement of the external neurostimulator 305 within the pouch 2090 is prevented. The cover 2094 is formed from a soft polyurethane material, and the substrate 2092 is formed from a breathable, non-woven polyester. The pouch 2090 may further include label 2096 for identification purposes. The cover 2094 includes two openings 2093A, 2093B therein, each opening configured to allow passage of a lead 111. The cover 2094 includes a flange 2098 that is configured to be adhered or attached to the substrate 2092 by means of a pressure-sensitive adhesive. The flange 2098 ensures that the cover 2094 does not peel away or delaminate from the substrate 2092 when the external neurostimulator 305 is inserted into the pouch 2090. A layer of acrylic based adhesive (not shown) may be utilized to attach the substrate 2092 directly to a patient's skin.

A representative method for operating a patient treatment system can include implanting a lead in a patient, and positioning the proximal portion of the lead into a channel of an external neurostimulator as described herein. In an embodiment, the proximal portion of the lead is positioned into a channel of the external neurostimulator while the corresponding side door of the channel is in the partially-opened or unlocked configuration. The method can further include sliding or otherwise positioning the proximal end portion of the lead axially into a channel or slot carried by the external neurostimulator. Once the lead is fully positioned into the channel of the external neurostimulator, as indicated by the notch of the channel that functions as a depth indicator as described herein, the corresponding side door of the external neurostimulator is closed or locked with the lead positioned within the channel.

In an embodiment, the external neurostimulator 305 is configured such that the spring-loaded pins 362A, 362B and the connection contacts 113 of the lead 111 disengage when the external neurostimulator 305 is in the partially-opened or unlocked configuration. A practitioner may initially place the external neurostimulator 305 into the partially-opened or unlocked configuration prior to insertion or placement of a lead into a respective channel 352A, 352B. After the leads 111 are positioned as desired within the respective channel 352A, 352B, the practitioner closes or locks the side doors 336A, 336B to engage the connection contacts 113 of the lead 111 with the spring-loaded pins 362A, 362B of the external neurostimulator 305. Once the side doors 336A, 336B are closed or locked, the bosses 380A, 380B apply pressure onto the respective proximal end portion of the leads to hold the leads 111 firmly in place. As such, to ensure that the first and second series of spring-loaded pins 362A, 362B electrically contact the connection contacts 113 of the lead 111, the lead 111 is properly positioned or aligned within the respective channel 352A, 352B and the side doors 336A, 336B are closed or locked to firmly secure the leads 111 in place. The leads 111 may be released or removed from the respective channel 352A, 352B by partially opening or unlocking the side doors 336A, 336B such that the spring-loaded pins 362A, 362B disengage from the connection contacts 113 of the lead 111.

While features of this disclosure are described in relation to an external neurostimulator having a housing that is configured to directly receive the proximal portions of one or more leads 111, it will be understood by one of ordinary skill in the art that features of the housing may alternatively be incorporated onto a connector such as second connector 122 of the cable assembly 120. For example, the locking mechanism between the hooks 372A, 372B and the recesses 374A, 374B, respectively, of the side doors described herein may be implemented onto the second connector 122.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An external neurostimulator comprising:
   a housing, wherein the housing includes
      a base housing including a surface configured to contact a patient's skin, and
      a top housing including a central portion, a first side door hingedly coupled to a first side of the central portion, and a second side door hingedly coupled to a second side of the central portion, wherein each of the first side door and the second side door include a channel formed thereon that is configured to directly receive a proximal end portion of an implantable lead and wherein each channel includes a series of longitudinally spaced-apart openings formed on the first side door and the second side door, respectively;

a power source disposed within the housing;

a pulse generator disposed within the housing, wherein the pulse generator is electrically coupled to the power source; and a first series and a second series of spring-loaded pins electrically coupled to the pulse generator, wherein the first series of spring-loaded pins extend through the series of longitudinally spaced-apart openings of the channel on the first side door and the second series of spring-loaded pins extend through the series of longitudinally spaced-apart openings of the channel on the second side door, wherein the base housing includes at least one press fit feature configured to mate with an opening formed on an underside surface of the central portion of the top housing such that the base housing is attached to the top housing via the press fit feature.

2. The external neurostimulator of claim 1, wherein each of the first side door and the second side door has a locked configuration and an unlocked configuration.

3. The external neurostimulator of claim 2, wherein the central portion of the top housing includes a first tab and a second tab, the first and second tabs opposing each other and including a hook formed on outermost end thereof, wherein in the locked configuration of the first side door, the hook of the first tab is received within a recess formed on an inner surface of the first side door, and wherein in the locked configuration of the second side door, the hook of the second tab is received within a recess formed on an inner surface of the second side door.

4. The external neurostimulator of claim 3, wherein each of the first side door and the second side door include a latch having an opening formed therethrough, each latch extending towards the base housing, and wherein the base housing includes a first post extending outwardly therefrom and a second post extending outwardly therefrom, the latch of the first side door being configured to receive the first post and the latch of the second side door being configured to receive the second post.

5. The external neurostimulator of claim 4, wherein the opening of each latch includes a top circular portion, a bottom circular portion, and a waisted portion disposed between the top and bottom circular portion, and wherein in the locked configuration of the first side door, the first post is disposed in the top circular portion of the opening of the latch of the first side door, and wherein in the locked configuration of the second side door, the second post is disposed in the top circular portion of the opening of the latch of the second side door, and wherein in the unlocked configuration of the first side door, the first post is disposed in the bottom circular portion of the opening of the latch of the first side door, and wherein in the unlocked configuration of the second side door, the second post is disposed in the bottom circular portion of the opening of the latch of the second side door.

6. The external neurostimulator of claim 3, wherein a boss is formed on each of the first tab and the second tab, each boss being configured to apply pressure onto the proximal end portion of the implantable lead when the first side door or the second side door, respectively, is in the locked configuration.

7. The external neurostimulator of claim 6, wherein a top surface of each boss is curved.

8. The external neurostimulator of claim 3, wherein the base housing includes a first snap fit feature and a second snap fit feature extending therefrom, the first snap fit feature configured to mate with an opening formed on an underside surface of the first tab of the central portion and the second snap fit feature configured to mate with an opening formed on an underside surface of the second tab of the central portion.

9. The external neurostimulator of claim 1, wherein the channel for each of the first side door and the second side door includes a first end and a second end opposing the first end, the first end being configured as a lead insertion entry point, wherein the first end of the channel for each of the first side door and the second side door includes a horseshoe-shaped surface protrusion formed adjacent thereto.

10. The external neurostimulator of claim 1, wherein the channel for each of the first side door and the second side door includes a first end, a second end opposing the first end, and a notch formed between the first end and the second end, the notch extending outwardly from a longitudinal axis of the channel and being configured as a lead depth indicator point.

11. The external neurostimulator of claim 1, wherein the channel for each of the first side door and the second side door includes a circular portion configured to receive the proximal portion of the implantable lead and a trapezoidal portion configured to receive a stylet.

12. The external neurostimulator of claim 1, wherein each spring-loaded pin of the first series and the second series of spring-loaded pins is configured to contact a connection contact of the proximal portion of the implantable lead.

13. The external neurostimulator of claim 1, wherein the housing has a height of between 18 mm and 22 mm.

14. The external neurostimulator of claim 1, wherein the base housing has a curved perimeter.

* * * * *